United States Patent
Wine

(10) Patent No.: US 12,377,024 B2
(45) Date of Patent: Aug. 5, 2025

(54) SEMI-AUTOMATED COMPOUNDING PLATFORM

(71) Applicant: CareFusion 303, Inc., San Diego, CA (US)

(72) Inventor: Jason Andrew Wine, Brea, CA (US)

(73) Assignee: CareFusion 303, Inc., San Diego, CA (US)

( * ) Notice: Subject to any disclaimer, the term of this patent is extended or adjusted under 35 U.S.C. 154(b) by 168 days.

(21) Appl. No.: 18/346,490

(22) Filed: Jul. 3, 2023

(65) Prior Publication Data
US 2025/0009603 A1    Jan. 9, 2025

(51) Int. Cl.
| A61J 1/20 | (2006.01) |
| A61J 3/00 | (2006.01) |
| A61M 39/22 | (2006.01) |
| B01F 31/00 | (2022.01) |
| B01F 35/513 | (2022.01) |
| B01F 101/22 | (2022.01) |

(52) U.S. Cl.
CPC ............ *A61J 3/002* (2013.01); *A61M 39/223* (2013.01); *B01F 31/00* (2022.01); *B01F 35/513* (2022.01); *B01F 2101/22* (2022.01)

(58) Field of Classification Search
CPC .................................. A61J 1/20; A61J 1/2037
See application file for complete search history.

(56) References Cited

U.S. PATENT DOCUMENTS 4,842,028 A    6/1989  Kaufman et al.
6,813,868 B2 *  11/2004  Baldwin .................... B65B 9/02
                                                   53/411
8,297,320 B2 *  10/2012  Giribona ............... B01F 35/146
                                                   141/2
2011/0004187 A1 *  1/2011  Beiriger ................. A61M 5/162
                                                   604/500
2015/0251778 A1 *  9/2015  Tachibana ............... B65B 3/003
                                                   141/2

(Continued)

FOREIGN PATENT DOCUMENTS

EP    2902002 A1    8/2015

OTHER PUBLICATIONS

International Search Report and Written Opinion for Application No. PCT/US2024/034526, dated Sep. 16, 2024, 11 pages.

*Primary Examiner* — Paul J Gray
(74) *Attorney, Agent, or Firm* — Maschoff Brennan

(57) ABSTRACT

A compounding platform including a compounding station having a user interface and a rotating device. The compounding platform including a chamber coupled to the compounding station. The rotating device is coupled to the chamber and configured to rotate the chamber relative to the compounding station. The compounding platform further including a consumable configured to be disposed within the chamber and including a plurality of ports and a bladder in fluid communication with the plurality of ports. The compounding platform has a first vial removably coupled to the consumable via a first port of the plurality of ports and including a diluent fluid, and a second vial removably coupled to the consumable via a second port of the plurality of ports and including a medicament. The compounding platform includes a plurality of valves configured to control fluid flow into and out of the bladder and corresponding to the plurality of ports.

19 Claims, 13 Drawing Sheets

(56) References Cited

U.S. PATENT DOCUMENTS

2021/0128411 A1* 5/2021 Kato .................... A61J 1/2065
2021/0308012 A1* 10/2021 Tagliamento ......... A61J 1/2062
2022/0031570 A1 2/2022 Marine et al.

* cited by examiner

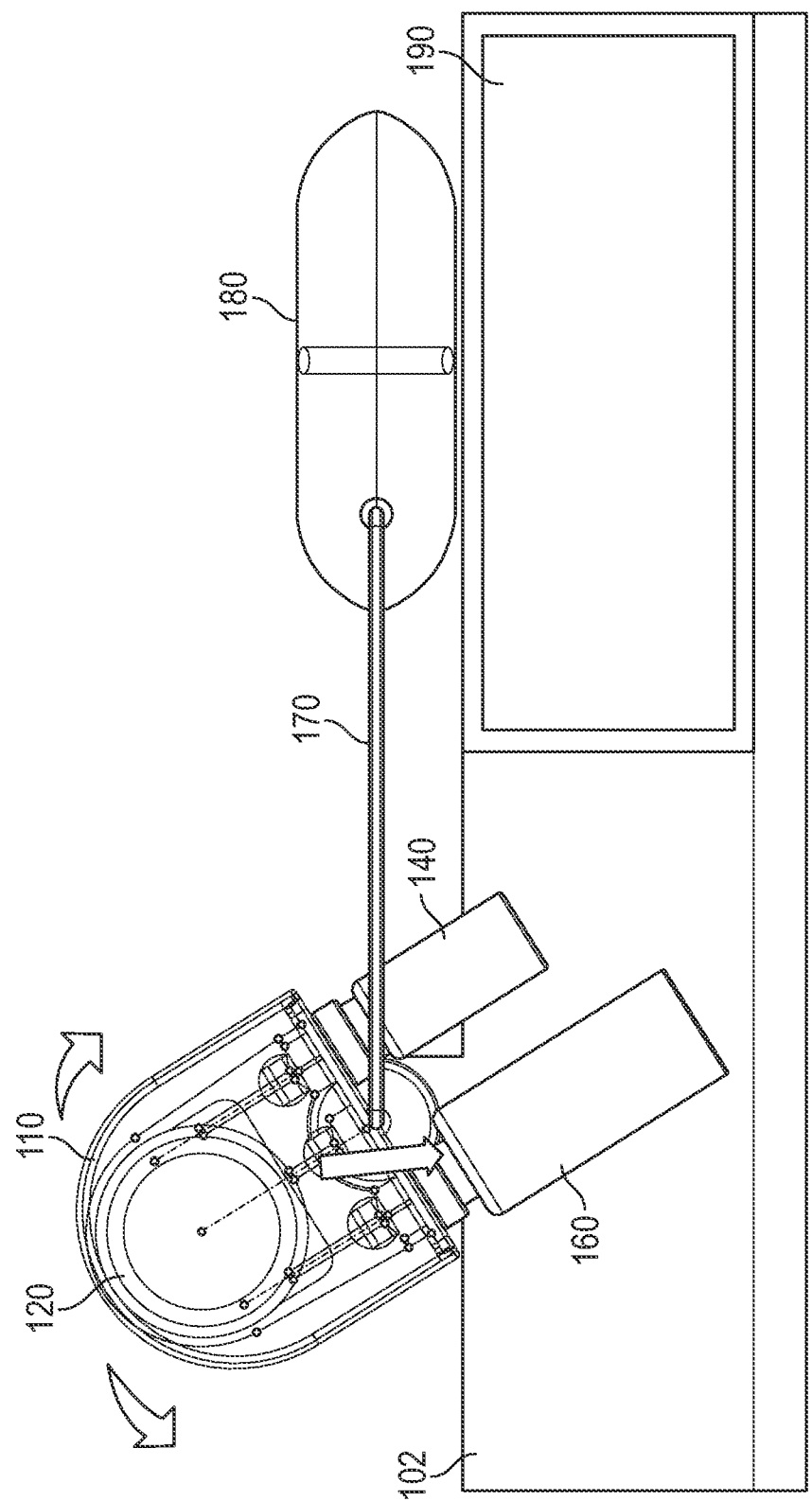

SEMI-AUTOMATED COMPOUNDING PLATFORM

FIELD OF THE INVENTION

The present disclosure generally relates to a semi-automated compounding platform, and, in particular, to a semi-automated compounding platform for the preparation of parenteral medications.

BACKGROUND

Medical treatments often include the infusion of a medical fluid (e.g., a saline solution or a liquid medication) to patients using an intravenous (IV) catheter that is connected though an arrangement of flexible tubing and fittings to a source of fluid, for example, an IV bag. Compounding platforms may be used for the preparation of parenteral medications for infusion.

Conventional compounding platforms may be manual or semi-automated. Conventional compounding platforms require many consumables to be used during preparation of infusion medications. In addition, conventional compounding platforms require many steps and/or procedures, which results in significant interaction by a user. Moreover, conventional compounding platforms require costly components, such as syringe pumps and complicated consumables, increasing the overall costs of the compounding platform.

SUMMARY

One or more embodiments of the present disclosure are directed a compounding platform including a compounding station including a user interface configured to receive inputs from a user and a rotating device, a chamber coupled to the compounding station, wherein the rotating device is coupled to the chamber and configured to rotate the chamber relative to the compounding station, a consumable configured to be disposed within the chamber, the consumable including a plurality of ports and a bladder in fluid communication with the plurality of ports;
 a first vial removably coupled to the consumable via a first port of the plurality of ports, the first vial including a diluent fluid, a second vial removably coupled to the consumable via a second port of the plurality of ports, the second vial including a medicament, and a plurality of valves configured to control fluid flow into and out of the bladder, wherein the plurality of valves correspond to the plurality of ports.

In some embodiments, the consumable includes a sealing element configured to allow the bladder to be in communication with the plurality of ports. The chamber includes a slot and the consumable is disposed through the slot such that the sealing element engages with the slot to secure the bladder within the chamber. The chamber is airtight upon inserting the consumable through the slot and disposing the sealing element within the slot. The sealing element includes the first port and the second port.

In some embodiments, the bladder includes a first flow path in fluid communication with the first port and a second flow path in communication with the second port. The plurality of valves includes a first valve and a second valve, the first valve configured to block flow within the first flow path and the second valve configured to block flow within the second flow path. The first flow path is in fluid communication with the first vial when the first vial is coupled to the first port. The second flow path is in fluid communication with the second vial when the second vial is coupled to the second port.

In some embodiments, the compounding platform further includes a delivery bag removably coupled to the consumable via a third port of the plurality of ports. The third port is coupled to a delivery tube, the delivery tube coupling the delivery bag to the third port.

In some embodiments, the compounding platform further includes a pressure device coupled to the chamber, the pressure device configured to generate a vacuum within the chamber.

In some embodiments, the compounding platform further includes a pressing device coupled to the chamber, the pressing device including a pressing face disposed within the chamber, the pressing device having a retracted position and an extended position, wherein in the extended position, the pressing device is proximate the bladder compared to when the pressing device is in the retracted position.

In some embodiments, the chamber is a vacuum chamber.

In some embodiments, the first port and the second port allow for two-way fluid communication.

In some embodiments, the bladder includes an interior space in fluid communication with the first vial and the second vial.

In some embodiments, the compounding platform further includes a controller disposed within the compounding station and communicatively coupled to the user interface, the controller configured to cause the compounding station to perform a set of maneuvers in response to the inputs received via the user interface, wherein the set of maneuvers includes one or more of rotation of the chamber, opening of one of the plurality of valves, and generation of a vacuum within the chamber.

In some embodiments, the rotating device rotates the chamber from 0 degrees to 360 degrees from a baseline position relative to the compounding station.

One or more embodiments of the present disclosure are directed a compounding platform including a compounding station including a user interface configured to receive inputs from a user and a rotating device, a chamber coupled to the compounding station and having a slot, wherein the rotating device is coupled to the chamber and rotates the chamber from 0 degrees to 360 degrees from a baseline position relative to the compounding station, a consumable configured to be disposed within the chamber, the consumable including a sealing element, a plurality of ports, and a bladder in fluid communication with the plurality of ports, wherein the chamber includes a slot and the consumable is disposed through the slot such that the sealing element engages with the slot to secure the bladder within the chamber, a first vial removably coupled to the consumable via a first port of the plurality of ports, the first vial including a diluent fluid, a second vial removably coupled to the consumable via a second port of the plurality of ports, the second vial including a medicament, wherein the bladder includes an interior space in fluid communication with the first vial and the second vial, a plurality of valves configured to control fluid flow into and out of the bladder, wherein the plurality of valves correspond to the plurality of port, a pressing device coupled to the chamber, the pressing device including a pressing face disposed within the chamber, the pressing device having a retracted position and an extended position, wherein in the extended position, the pressing device is proximate the bladder compared to when the pressing device is in the retracted position, a pressure device coupled to the chamber, the pressure device configured to generate a vacuum within the chamber, and a delivery bag removably coupled to the consumable via a third port of the plurality of ports, wherein the bladder includes a first flow path in fluid communication with the first port and a second flow path in communication with the second port, and the plurality of valves includes a first valve and a second valve, the first valve configured to block flow within the first flow path and the second valve configured to block flow within the second flow path.

One or more embodiments of the present disclosure are directed to a method of compounding a medical fluid, the method including inserting a consumable through a slot of a chamber to dispose the consumable within the chamber, the consumable including a bladder configured to expand, generating a vacuum within the chamber to cause an inflow of air to enter the consumable through a first port, removably coupling a first vial the chamber, the first vial containing a medicament fluid and being in fluid communication with the first port of the consumable when coupled to the chamber to allow the medicament fluid to flow from the first vial to the bladder, rotating the chamber to cause the air from the consumable to flow into the first vial via the first port, which causes a predetermined amount of the medicament fluid to flow from the first vial into the consumable, and closing the first port and opening a second port coupled to a delivery bag such that the predetermined amount of medicament fluid flows through the second port to the delivery bag.

One or more embodiments of the present disclosure are directed to a method of reconstituting a medical fluid, the method including generating a vacuum within a chamber, the chamber coupled to a compounding station and including a consumable having a first port and a second port, wherein the generation of the vacuum causes an inflow of air to enter the consumable and the first port and the second port are in fluid communication with the consumable, removing the vacuum from the chamber and opening a first valve of a plurality of valves to cause the air to flow from the consumable into a first vial resulting in diluent fluid flowing from the first vial to the consumable through the first port, the first vial coupled to the first port such that the first vial is in fluid communication with the consumable when the first valve is opened, rotating the chamber, via a rotating device coupling the chamber to the compounding state, such that the chamber is substantially inverted from a baseline position, in response to rotating the chamber, opening a second valve of the plurality of valves to cause the diluent fluid to flow from the consumable to a second vial, the second vial coupled to the second port such that the second vial is in fluid communication with the consumable when the second valve is opened, the second vial including a medicament, oscillating the chamber, via the rotating device, such that that second vial is oscillated causing the medicament to at least partially dissolve in the diluent fluid within the second vial to create a reconstituted fluid, and rotating the chamber, via the rotating device, to the baseline position causing the reconstituted fluid to flow from the second vial to the consumable via the second port.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 4C is a front view of the compounding platform of FIG. 1A with the compounding platform in use, in accordance with various aspects of the present disclosure.

DETAILED DESCRIPTION

Figure 1A:
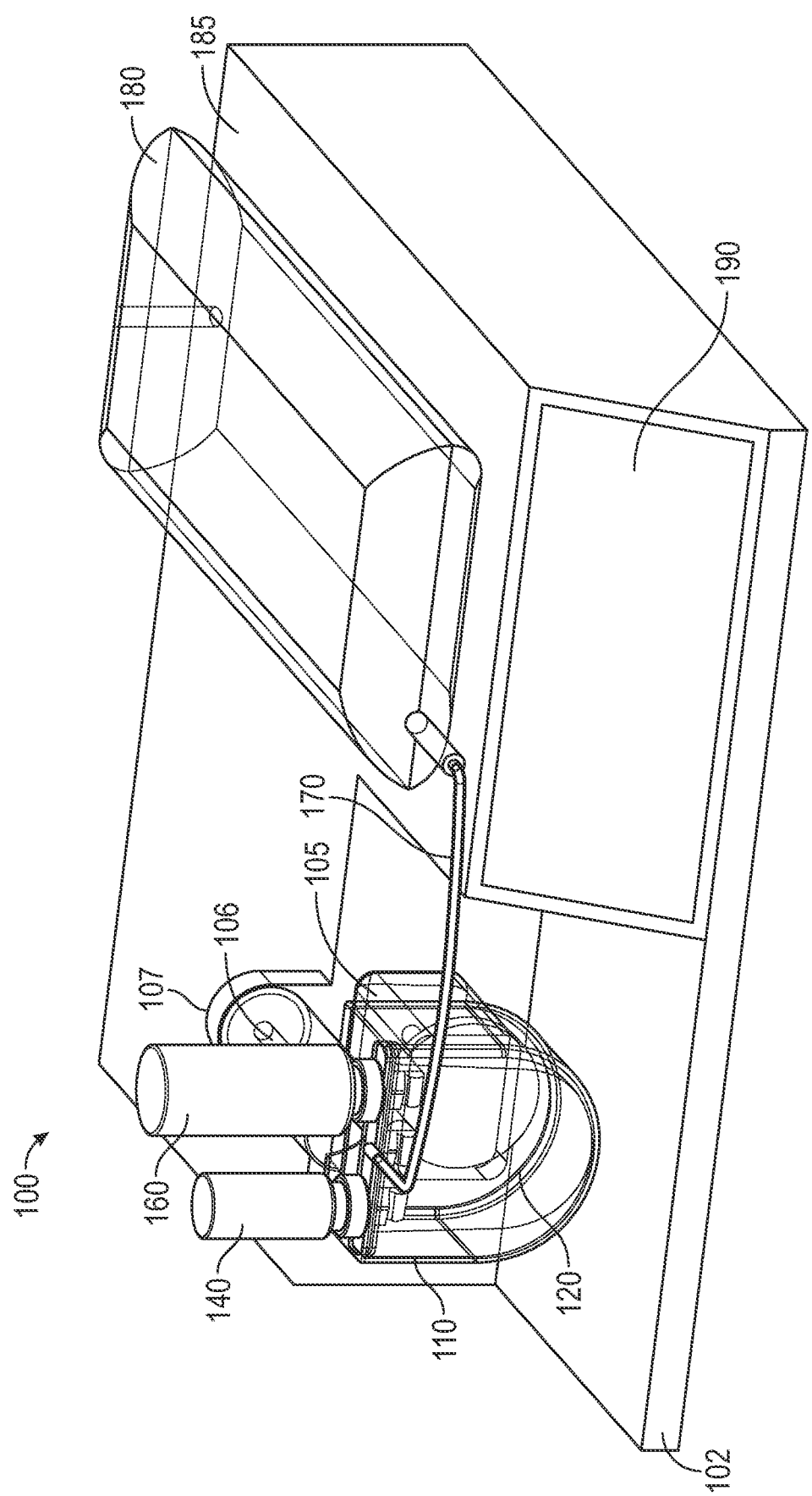
FIG. 1A is a front perspective view of a compounding platform, in accordance with various aspects of the present disclosure.

The disclosed compounding platform allows for the movement of a quantified amount of fluid from one or more vials to a final delivery container or bag. The term fluid herein may refer to any type of fluid, such as a liquid or a gas. The compounding platform allows for the mixing of a diluent and medication by selectively controlling the flow path of fluid from a vial to the delivery bag. In some embodiments, the compounding platform controls the ratios of diluent to medication such that a user can specify a specific ratio of diluent to medication to be delivered to a delivery bag. The delivery bag may be used to store medical fluid to be delivered to a patient, such as via infusion. The delivery bag may include a medical fluid titrated and/or compounded by compounding platform for delivery to a patient.

The compounding platform includes a compounding station, a consumable, and a delivery bag. The consumable is coupled to the compounding station such that the compounding station controls the flow of fluid into and out of the consumable. The compounding station can include a chamber configured to receive the consumable. For example, the consumable may be placed within the chamber of the compounding station and various pumps or valves may be connected to the consumable to control the flow of fluid into and out of the consumable. The consumable is further coupled to the delivery bag. In some embodiments, the consumable is coupled to the delivery bag via tubing, such as a delivery tube.

The consumable includes one or more ports, including inlets, and outlets. The ports of the consumable are configured to couple to one or more vials to allow fluid to flow from the vial into the consumable. For example, the consumable may include a bladder that fills up with fluid from the vial coupled to a port. The port may allow for two way fluid flow. For example, the port may allow fluid to flow into the bladder of consumable and out of the bladder. The consumable may include a port allowing for fluid to flow from the bladder to the delivery bag via a delivery tube.

In some embodiments, the consumable is disposed within the chamber of the compounding station. The compounding station may include a pressure device coupled to the chamber. The pressure device may be configured to generate a vacuum within the chamber. The chamber may be a vacuum chamber and a vacuum may be applied to the bladder when the consumable is disposed within the chamber. In some embodiments, insertion of the consumable within the chamber seals the chamber to allow a vacuum to be applied within the chamber. Further, application of vacuum may be used to control the flow fluid into bladder. For example, to pull fluid into the bladder, a desired flow path is set to open via a valve coupled to one of the ports of the consumable. The other ports may remain closed. A vacuum is applied to the chamber pulling fluid into the bladder.

The compounding station includes one or more device to interact with the consumable and/or the bladder. For example, the compounding station may include a pressing device and a rotating device. The pressing device may be a linear actuator having a press face. The pressing face is disposed within the chamber and is configured to push against the bladder of the consumable to prevent over expansion of the bladder. For example, to control the volume of the fluid pulled into the bladder, the pressing device positions the press face proximate to the bladder to create an expansion boundary or limit. The position of the press face can be adjusted based on the amount of volume expected to flow into the bladder. The compounding platform can apply a vacuum within the chamber and position the press face such that the desired volume is pulled into the bladder.

The rotating device is coupled to the chamber and is configured to rotate the chamber. For example, the rotation device can rotate the chamber to allow for fluid to flow from one or more vials coupled to the consumable to into the bladder with the assistance of gravity. The rotation device is configured to allow rotation of the chamber and consumable relative to the compounding station and the delivery bag. In some embodiments, the rotating device allows for a rocking or shaking motion of the chamber to allow for mixing of fluids within the bladder.

The compounding station can include one or more valves or pumps coupled to each port. For example, each port of the consumable may have a corresponding valve coupled to it to a control the opening and closing of the port. The valve may control the flow of fluid from a vial coupled to the port to into the bladder. Compounding station may include a processor (e.g., controller), such as a microcontroller, configured to control various aspects and devices of compounding platform, such as the rotation device and the pressing device.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the preparation of medical fluids by a compounding platform to be delivered to a patient, it is to be understood that this description is only an example of usage and does not limit the scope of the claims. Various aspects of the disclosed compounding system may be used in any application where it is desirable to provide medical fluids to a patient.

The disclosed compounding platform overcomes several challenges discovered with respect to certain conventional compounding platforms. One challenge with certain conventional compounding platforms is that certain conventional compounding platforms may be cumbersome to use or may require expensive components. For example, certain conventional compounding platform require significant interaction by a user or require expensive components. Therefore, in accordance with the present disclosure, it is advantageous to provide compounding platforms as described herein that allows for improved compounding of medical fluid.

Figure 1B:
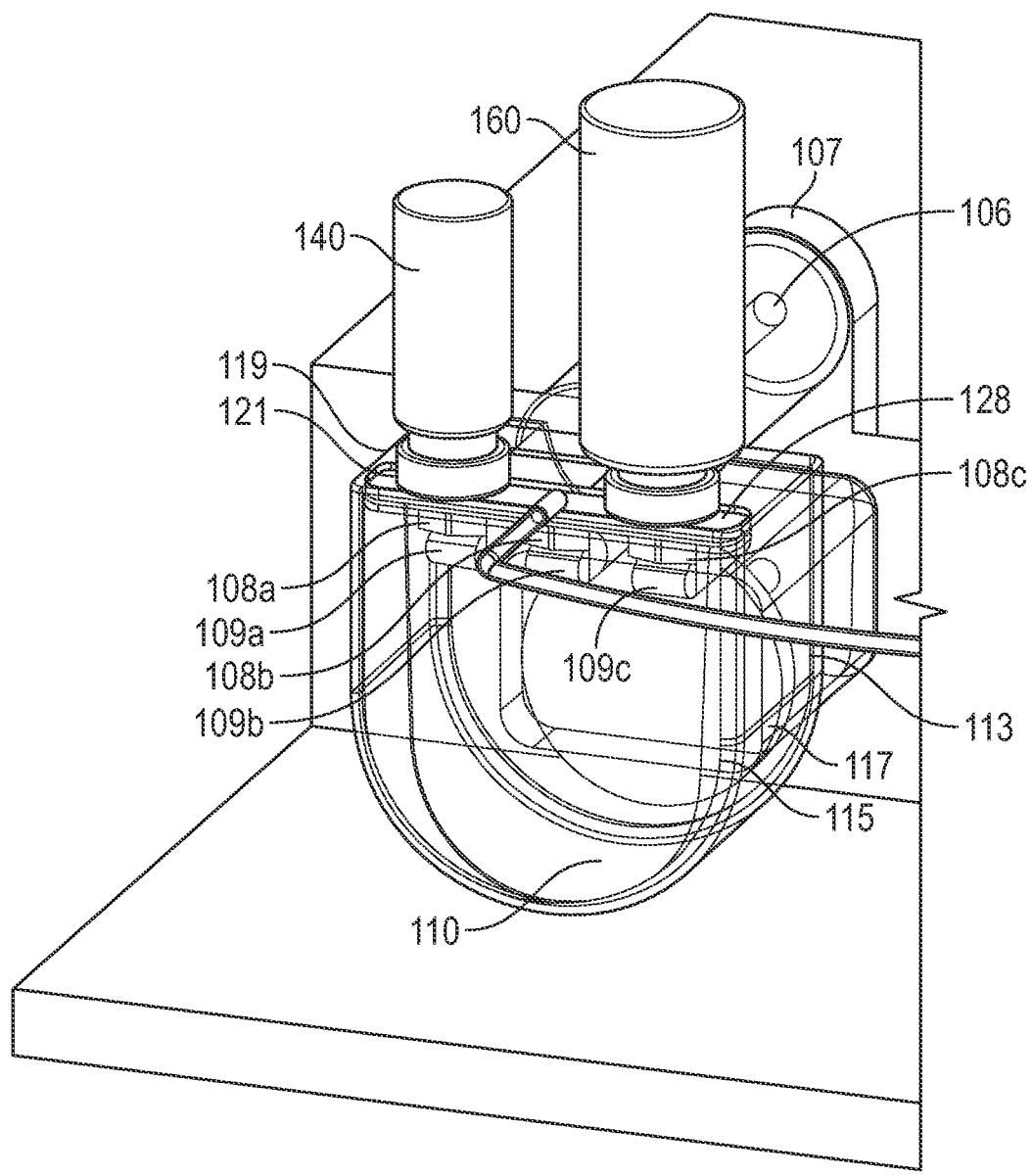
FIG. 1B is a zoomed in front perspective view of a consumable of the compounding platform of FIG. 1A, in accordance with various aspects of the present disclosure.
Figure 1C:
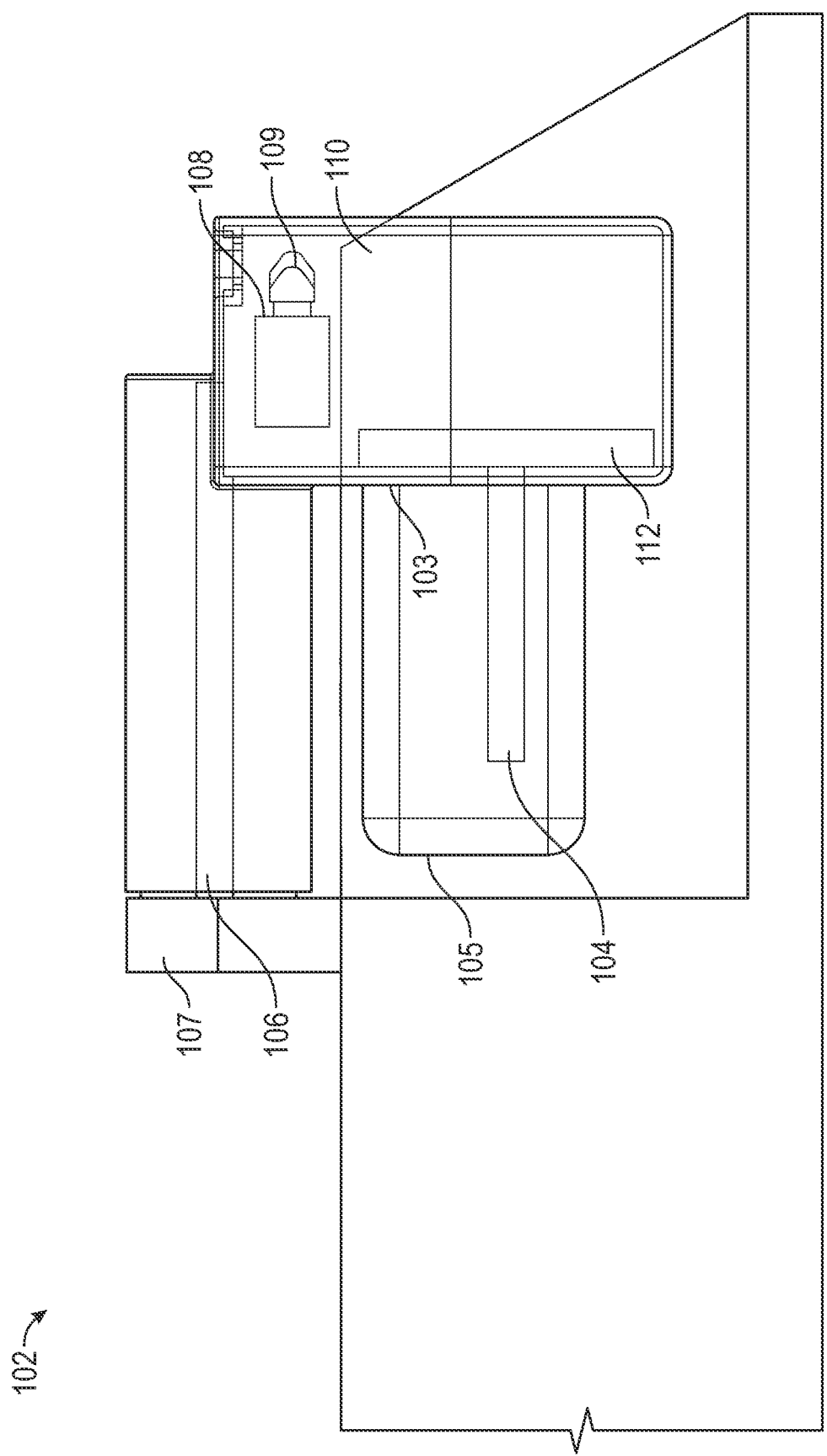
FIG. 1C is a side in view of the compounding platform of FIG. 1A, in accordance with various aspects of the present disclosure.

FIG. 1A is a front perspective view of a compounding platform, in accordance with various aspects of the present disclosure. FIG. 1B is a zoomed in front perspective view of a consumable of the compounding platform of FIG. 1A, in accordance with various aspects of the present disclosure. FIG. 1C is a side in view of the compounding platform of FIG. 1A, in accordance with various aspects of the present disclosure.

With reference to FIGS. 1A-1C, compounding platform 100 allows for preparation of fluids (e.g., medical fluids) for delivery to a patient. For example, compounding platform 100 may allow for preparation of parenteral drugs for delivery to a patient. The term fluid herein may refer to any type of fluid, such as a liquid or a gas. Compounding platform 100 may prepare the fluid (e.g., medical fluid) and store the prepared fluid within a container, such as delivery bag 180. The container may be infused to a patient or coupled to a patient via one or more catheters or needles.

Compounding platform 100 may include compounding station 102, chamber 110, storage area 185, and user interface 190. User interface 190 may be used to control compounding station 102. For example, a user may interact with user interface 190 to specify parameters for preparation of a medical fluid. The medical fluid may be prepared by compounding platform 100 and stored within delivery bag 180 such that the medical fluid can be delivered to a patient. User interface 190 may receive inputs from a user and may include a touchscreen, keyboard, buttons, switches, or other input mechanisms.

In some embodiments, compounding station 102 includes a controller, such as a microcontroller, configured to control one or more processes of compounding station 102. For example, the controller may be coupled to user interface 190 and is configured to receive inputs form user interface 190 and control one or more other devices or components of compounding station 102 to prepare a medical fluid.

In some embodiments, compounding platform 100 includes chamber 110. Chamber 110 may be coupled to compounding station 102. Chamber 110 may be configured to receive a consumable (e.g., consumable 120). Chamber 110 may be a vacuum chamber configured to contain a vacuum when consumable 120 is disposed within. Chamber 110 may be coupled to compounding station 102 such that chamber 110 is rotatable relative to compounding station 102.

In some embodiments, storage area 185 is configured to store delivery bag 180. Delivery bag 180 may be a container for storing a medical fluid. Delivery bag 180 may be coupled to consumable 120 disposed within chamber 110. Delivery bag 180 may be coupled to consumable 120 via delivery tube 170, for example. In some embodiments, delivery tubing 170 is removable coupled to delivery bag 180 and/or consumable 120.

In some embodiments, delivery tube 170 allows delivery bag 180 to be in fluid communication with consumable 120. In use, delivery bag 180 may contain a medical fluid to be delivery to a patient. For example, delivery bag 180 may include a medical fluid to be infused with a delivery line to a patient. Delivery tube 170 may be configured to be decoupled form delivery bag 180. For example, upon completion of the storage of the desired fluid within delivery bag 180 via compounding station 102, delivery tubing 170 may be decoupled from delivery bag 180 to allow delivery bag 180 to be transported to another location for use.

The medical fluid may be a combination of a diluent and drug. In some embodiments, compounding platform 100 is configured to prepare a medical fluid by selectively controlling the flow of a diluent and a drug into consumable 120, which may then flow to delivery bag 180. For example, compounding station 102 may be configured to selectively control one or more valves or pumps to control the flow of fluid to and from a fluid source (e.g., a diluent vial and/or a drug vial) to consumable 120 stored within chamber 110.

In some embodiments, consumable 120 is disposed within chamber 110 and is coupled to one or more vials. For example, consumable 120 may be coupled to first vial 140 and second vial 160. In some embodiments, first vial 140 is a vial containing diluent fluid and second vial 160 is a vial containing a drug, such as a lyophilized drug. Consumable 120 may be in fluid communication with first vial 140 and second vial 160. Consumable 120 may be substantially airtight.

Chamber 110 may include proximal wall 113, distal wall 115, sidewall 117, top wall 119. Sidewall 117 may be disposed between proximal wall 113 and distal wall 115 such that sidewall 117 couples proximal wall 113 to distal wall 115. Sidewall 117 may extend a majority of the perimeter of chamber 110. In some embodiments, top wall 119 extends between proximal wall 113 and distal wall 115. Top wall 119 may extend from one end of sidewall 117 to another end of sidewall 117. For example, sidewall 117 may be substantially semi-circular and top wall 119 may connect to the ends of sidewall 117. In some embodiments, top wall 119 includes slot 121. Slot 121 may be configured to receive consumable 120. For example, consumable 120 may be inserted through slot 121 to dispose consumable 120 within chamber 110. In some embodiments, slot 121 secures consumable 120 in place within chamber 110. Slot 121 may be configured to couple to sealing element 128 of consumable 120 to secure consumable within slot 121. Slot 121 may allow consumable 120 to be secured within chamber 110 and provide an airtight seal between consumable 120 and chamber 110. In other words, slot 121 may form an airtight seal with sealing element 128 when consumable 120 is disposed through slot 121 and into chamber 110.

In some embodiments, slot 121 is disposed proximate distal wall 115. Slot 121 being disposed distal wall 115 results in consumable 120 being proximate distal wall 115 when consumable 120 is disposed within chamber 110. In some embodiments, when consumable 120 is disposed within chamber 110, consumable 120 may be proximate sidewall 117 and distal wall 115. For example, a perimeter of consumable 120 may be substantially parallel to sidewall 117 and may be disposed proximate sidewall 117. In some embodiments, the contour of the perimeter of consumable 120 corresponds with the contour of sidewall 117.

In some embodiments, chamber 110 includes one or more valves or pumps (e.g., valves 109a, 109b, 109c) configured to control the flow of fluid to and from consumable 120. For example, valve 109a may be controlled by motor 108a and may be configured to control the flow of fluid from first vial 140 into and out of consumable 120. Valve 109b may be controlled by motor 108b and may be configured to control the flow of fluid from consumable 120 (e.g., through port 126) to delivery bag 180 via delivery line 170. Valve 109c may be controlled by motor 108c and may be configured to control the flow of fluid from second vial 160 into and out of consumable 120. Each valve 109a, 109b, and 109c has a corresponding motors 108a, 108b, 108c that controls the valve as described in detail below.

In some embodiments, compounding station 102 includes rotating device 107 and pressure device 106. Rotation device 107 may include a motor and may be configured to rotate chamber 110 with respect to compounding station 102. For example, rotation device 107 may be coupled to chamber 110 and configured to rotate 360 degrees relative to compounding station 102 such that chamber 110 rotates relative to compounding station 102. In some embodiments, rotating device 107 allows chamber 110 to rotation 360 degrees relative to compounding station 102. For example, chamber 110 may have a baseline position (e.g., 0 degrees) and may be rotated by rotating device 107 from the baseline position. In some embodiments, the baseline position of chamber 110 is such that fluid within bladder 130 of consumable 120 is disposed, due to gravity, opposite sealing element 128 and/or the vials coupled to consumable 120. For example, when chamber 110 is in the baseline position, any fluid disposed within consumable 120 is furthest from sealing element 128, any ports, or any vials coupled to consumable 120.

Rotating device 107 may be disposed proximate pressure device 106. In some embodiments, pressure device 106 is disposed within or through rotation device 107. For example, rotating device 107 may be coupled to chamber 110 and pressure device 106 may be disposed within and along rotating device 107.

In some embodiments, pressure device 106 controls the pressure within chamber 110. Pressure device 106 may include an air tube or channel coupled to chamber 110 and configured to add air or remove air from within chamber 110 to increase or decrease the pressure within chamber 110. In some embodiments, pressure device 106 is configured to remove all the air form within chamber 110 to generate a vacuum within chamber 110. Pressure device 106 may be coupled to chamber 110 such that pressure device 106 forms an airtight seal with chamber 110 to allow for generation of a vacuum within chamber 110. The generation of vacuum within chamber 110 may cause fluid, such as air or a liquid, to be driving into a bladder (e.g., bladder 130) disposed within chamber 110. For example, generation of a vacuum within chamber 110 may cause an inflow of air to enter consumable 120. The vacuum may be removed from chamber 110 resulting in the bladder remaining filled with the fluid. In other words, a vacuum may be used to drive fluid into a bladder disposed within chamber 110.

In some embodiments, compounding station 102 includes pressing device 105. Pressing device 105 may be a linear actuator and may include pressing face 112. Pressing device 105 may be disposed proximate rotating device 107 and/or pressure device 106. In some embodiments, pressing face 112 is disposed within chamber 110. Pressing device 105 is configured to extend and retract pressing face 112. For example, pressing device 105 and pressing face 112 may have an initial position (FIG. 3A), a partially extended position (FIG. 3B), and fully extended position (FIG. 3C). In some embodiments, the partially extended position is where pressing face 112 is between the initial position and the fully extended position. In the initial position, pressing face 112 is fully retracted such that it is forms an interior surface of chamber 110.

Pressing face 112 may extend into chamber 110 from the initial position. For example, pressing face 112 may be substantially flush with proximal wall 113 when pressing face 112 is in the initial position. In some embodiments, pressing face 112 contacts or is proximate proximal wall 113 when pressing face 112 is in the initial position. In some embodiments, pressing device 105 includes rod 104. Rod 104 may be configured to couple pressing face 112 to a motor of pressing device 105. For example, extension of rod 104 may cause pressing face 112 to extend from the initial position to the fully extended position.

Pressing device 105 may be configured to extend pressing face 112 towards distal wall 115. For example, in the initial position pressing face 112 may abut or may be proximate proximal wall 113 compared to distal wall 115, and in the partially extended position, pressing face 112 may extend away from proximal wall 115 such that pressing face is disposed between proximal wall 113 and distal wall 115. In some embodiments, when pressing face 112 is in the partially extended position, pressing face 112 is proximate distal wall 115 compared to when pressing face 112 is in the initial position. When pressing face 112 is in the fully extended position, pressing face 112 may abut consumable 120, such that consumable 120 is devoid of fluid. Pressing face 112 being in the fully extended position results in pressing face 112 pressing consumable 120 against distal wall 115. As described below, pressing face 112 being in the fully extended position causes fluid to flow out of consumable 120 due to consumable 120 being pressed against pressing face 112 and distal wall 115.

Chamber 110 may include opening 103 that allows chamber 110 to be in fluid communication with pressing device 107. Opening 103 may be disposed on proximal wall 113. Pressing face 112 may substantially seal opening 103 when pressing device 112 is in the initial position. As pressing face 112 extends towards distal wall 115, pressing face 112 may move away from opening 103, causing opening 103 to no longer be sealed by pressing face 112. In some embodiments, pressing device 107 is in fluid communication with chamber 110 via opening 103, such that a vacuum applied to chamber 110 results in a vacuum being applied to pressing device 107.

Figure 2A:
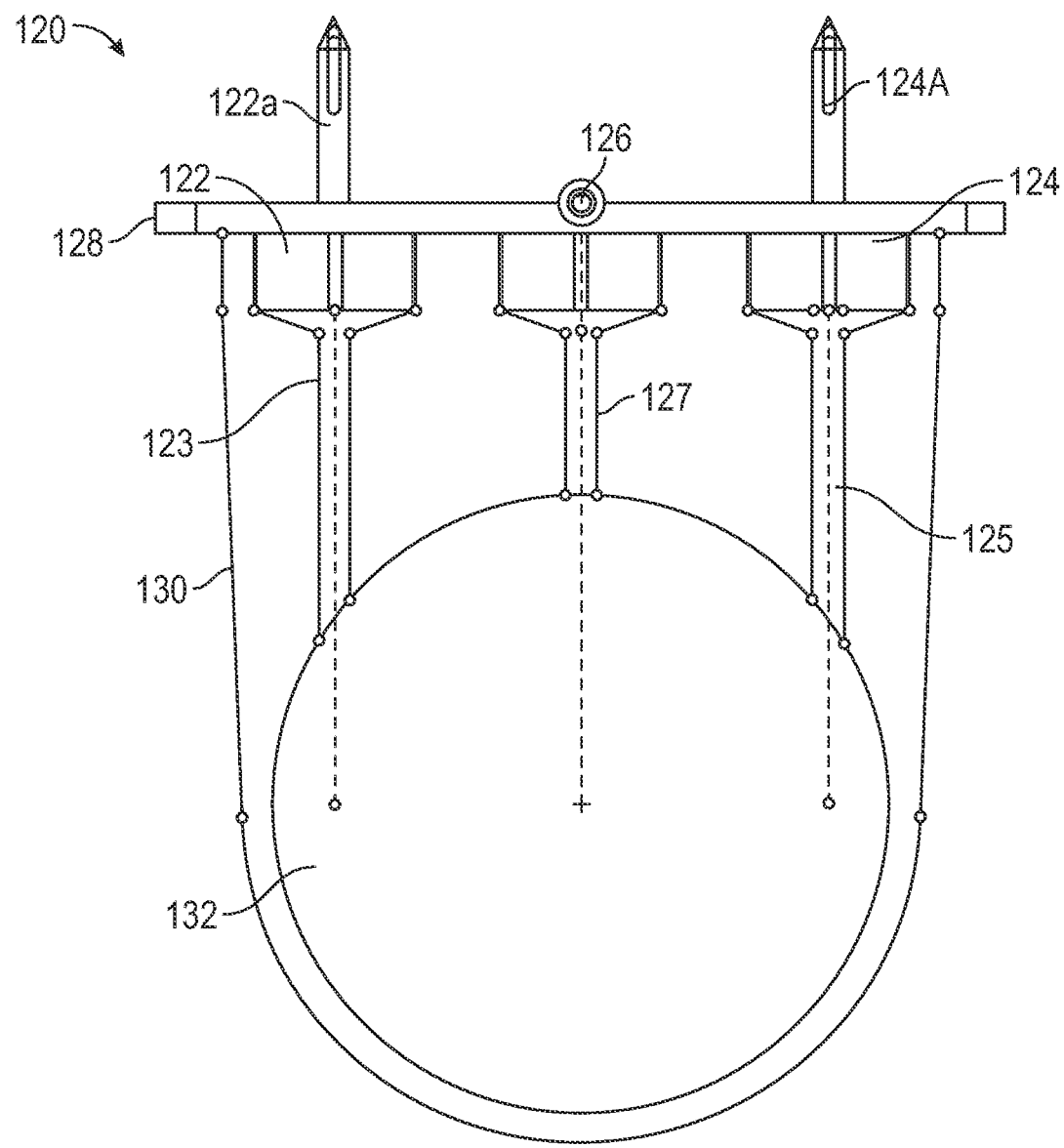
FIG. 2A is a front view of a consumable of the compounding platform of FIG. 1A, in accordance with various aspects of the present disclosure.
Figure 2B:
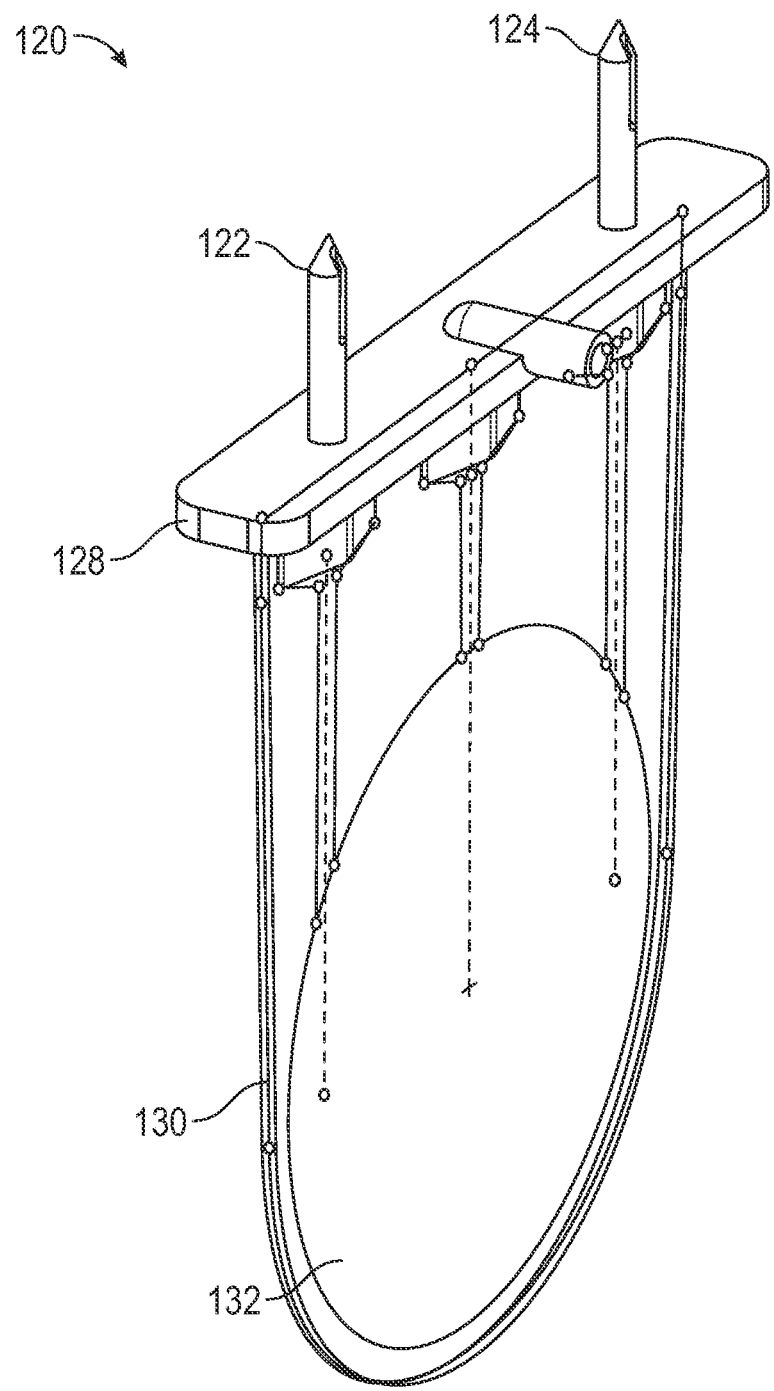
FIG. 2B is a perspective side view of the consumable of FIG. 2A, in accordance with various aspects of the present disclosure.

FIG. 2A is a front view of a consumable of the compounding platform of FIG. 1A, in accordance with various aspects of the present disclosure. FIG. 2B is a perspective side view of the consumable of FIG. 2A, in accordance with various aspects of the present disclosure.

Referring to FIG. 2A-2B, consumable 120 may include sealing element 128 and bladder 130. Bladder 130 may be coupled to sealing element 128. In some embodiments, bladder 130 is heat sealed to sealing element 128 such that consumable 120 remains substantially airtight. Consumable 120 may include ports 122, 124, 126. In some embodiments, ports 122, 124, 126, are configured to allow fluid to flow into and out of bladder 130. Each of port 122, 124, and 126 may be disposed on sealing element 128. Consumable 120 may be comprised of plastic or a polymer. In some embodiments, sealing element 128 is comprised of a hard plastic and bladder 130 is comprised of a plastic film. Sealing element 128 may be coupled to bladder 130 such that consumable 120 is airtight.

Port 122 and port 124 may be coupled to a fluid source. For example, port 122 may be coupled to first vial 140 and port 124 may be coupled to second vial 160. Port 122 and port 124 may include needle 122a and 124a, respectively. Needle 122a may extend from port 122 and needle 124a may extend from port 124. Needle 122a and needle 124a may be configured to extend into a vial of fluid when the vial of fluid is coupled to port 122 and port 124, respectively. Needle 122a and needle 124a may extend from sealing element 128. In use, a fluid source is coupled to port 122 and/or port 124 and needle 122a and/or 124a extend from port 122 and/or 124 and into the fluid source. In some embodiments, port 122, 124, 126 include any type of coupling mechanism to allow a fluid source to couple to port 122, 124, 126. For example, port 122, 124, 126 may each include a connection interface to allow for optimized and easy between port 122, 124, 126 and a fluid source.

Port 126 may be configured to couple to delivery tube 170 to allow fluid to flow from bladder 130 to delivery bag 180. In some embodiments, port 126 is a one-way outlet configured to allow fluid to flow from bladder 130 to delivery bag 180, without allowing fluid to flow from delivery bag 180 to bladder 130. Alternatively, port 126 is a two-way valve allowing for to and from delivery bag 180 and bladder 130. In some embodiments, an axis of port 126 is arranged perpendicular to the axis of port 122 and/or port 124. For example, an axis extending through port 122 and/or 124 may extend into bladder 130 and may be parallel to bladder 130. An axis extending through port 126 may be perpendicular to bladder 130 and parallel to the plane of sealing element 128. In some embodiments, a plane extending through at least a majority of bladder 130 is substantially perpendicular to a plane extending through at least a majority of sealing element 128.

In some embodiments, consumable 120 includes flow path 123, 127, and 125 extending into bladder 130 from port 122, 126, and 124, respectively. Each of flow path 123, 127, and 125 may be created via heat sealing portions of bladder 130. For example, portions of bladder 130 proximate ports 122, 124, 126 proximate sealing element 128 may be heat sealed to create flow path 123, 127, and 125. Flow path 123 may extend from port 122, flow path 127 may extend from port 126 and flow path 125 may extend from port 124. Flow path 123, 127, and 125 may direct the flow of fluid from port 122, 126, and 124, respectively, into and out of bladder 130. In some embodiments, flow path 123 and flow path 125 are inlet flow paths directing flow from a fluid source into bladder 130 and flow path 127 is an outlet flow path directing flow from bladder 130 to a fluid container (e.g., delivery bag 180).

In some embodiments, valves 109a, 109b, 109c are configured to control the flow of fluid (e.g., gas or liquid) through flow path 123, 127, and 125, respectively. Valve 109a may be in an open position allowing fluid to flow through flow path 123. Valve 109a being in the closed position may seal flow path 123 preventing fluid from flowing through flow path 123 and into or out of bladder 130. Valve 109b may be in an open position allowing fluid to flow through flow path 127. Valve 109b being in the closed position may seal flow path 127 preventing fluid from flowing through flow path 127 and into or out of bladder 130. Valve 109c may be in an open position allowing fluid to flow through flow path 125. Valve 109c being in the closed position may seal flow path 125 preventing fluid from flowing through flow path 125 and into or out of bladder 130.

In some embodiments, one or more of valves 109a, 109b, 109c is configured to control the flow of air into bladder 130. For example, valve 109a and/or valve 109c may pull air into bladder 130 prior to attachment of vial 140 and/or vial 160. In some embodiments, air is pulled into bladder 130 due to pressing device 107 generating a vacuum within chamber 110. For example, pressing device 107 may generate a vacuum within chamber 110 causing air to flow into bladder 130 through one or more of valves 109a, 109b, 109c, thus causing bladder 130 to expand.

Valves 109a, 109b, 109c may be a solenoid valve or plunger configured to extend and retract to control flow through flow path 123, 127, and 125. For example, valves 109a, 109b, 109c may extend outward to seal flow path 123, 127, and 125, respectively, and may retract inward to open flow path 123, 127, and 125, respectively, to allow fluid to flow through flow path 123, 127, and 125. In some embodiments, motors 108a, 108b, 108c and/or valves 109a, 109b, 109c extend into chamber 110. For example, motors 108a, 108b, 108c and/or valves 109a, 109b, 109c may extend into chamber 110 such that motors 108a, 108b, 108c and/or valves 109a, 109b, 109c are proximate consumable 120 when consumable 120 is disposed within chamber 110.

Valves 109a, 109b, 109c may be coupled to a microcontroller disposed within compounding station 102. The microcontroller may be configured to control the extension and retraction of valves 109a, 109b, 109c. In some embodiments, compounding station 102 is configured to run or go through predefined steps (e.g., rotation of chamber 110, actuation of pressure device 105 and/or pressing device 107) based on a program executed by the microcontroller.

In some embodiments, bladder 130 includes interior space 132. Interior space 132 may be configured to fill with fluid when fluid enters bladder 130 via ports 122, 124, and/or 126. In some embodiments, interior space 132 is formed via heat sealing a portion of bladder 130. Interior space 132 may be a defined portion of bladder 130 configured to expand and contract. For example, interior space 132 may expand when bladder 130 receives fluid and may contract when fluid flows out of bladder 130. Interior space 132 and bladder 130 may be substantially airtight. In some embodiments, bladder 130 is comprised of two plastic films sealed together along their perimeter to form an airtight bladder. When bladder 130 is substantially contracted such that bladder 130 is substantially devoid of fluid, the two plastic films comprising bladder 130 may be in contact. As bladder 130 receives and fills with fluid, the two plastic films may be spaced apart. The amount of fluid bladder 130 is able to hold is determined on the size of interior space 132. For example, the greater the volume of interior space 132, the greater volume of fluid bladder 130 can hold.

Figure 3A:
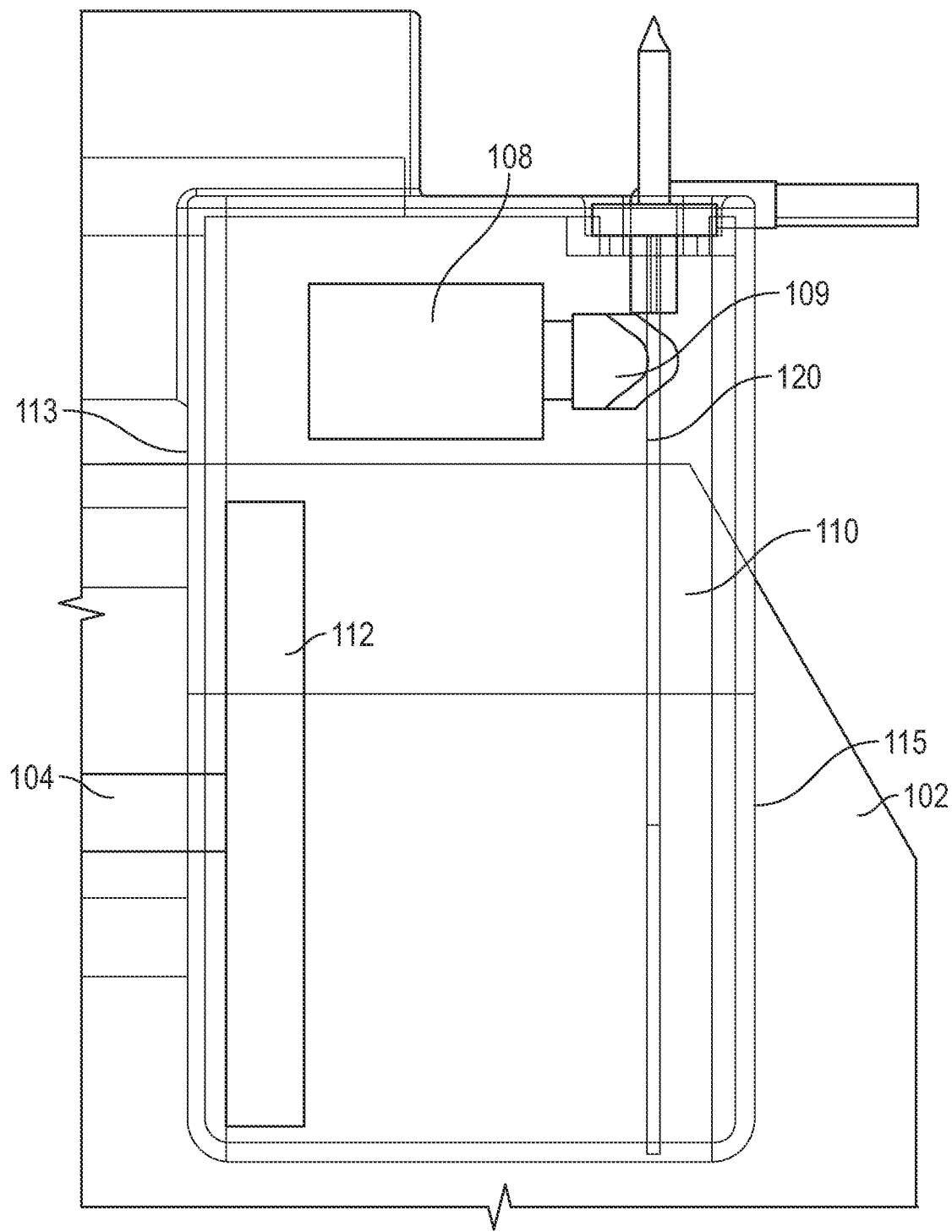
FIG. 3A is a zoomed in side view of the compounding platform of FIG. 1A with a pressing device in an initial position, in accordance with various aspects of the present disclosure.
Figure 3B:
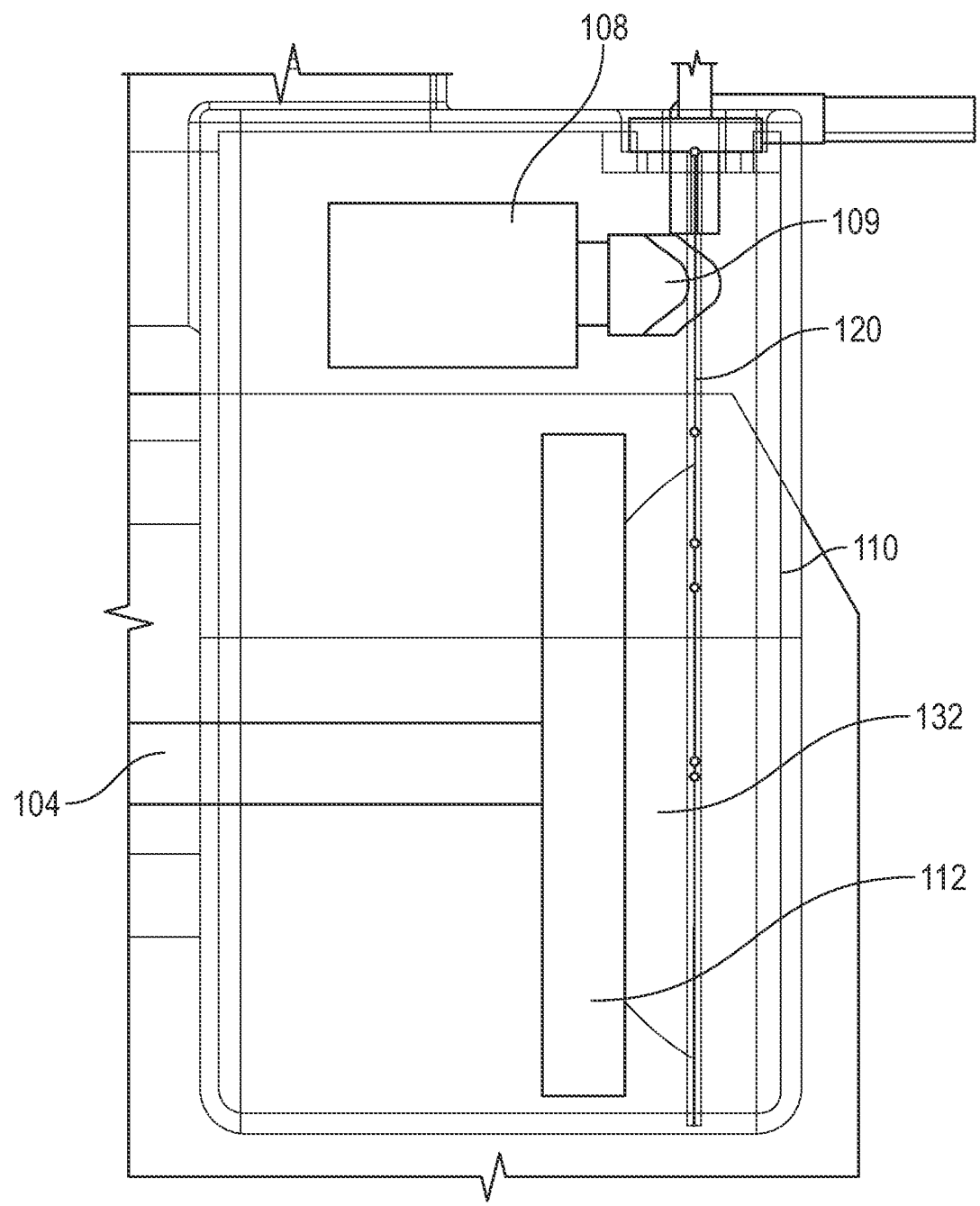
FIG. 3B is a zoomed in side view of the compounding platform of FIG. 1A with the pressing device in a partially extended position, in accordance with various aspects of the present disclosure.
Figure 3C:
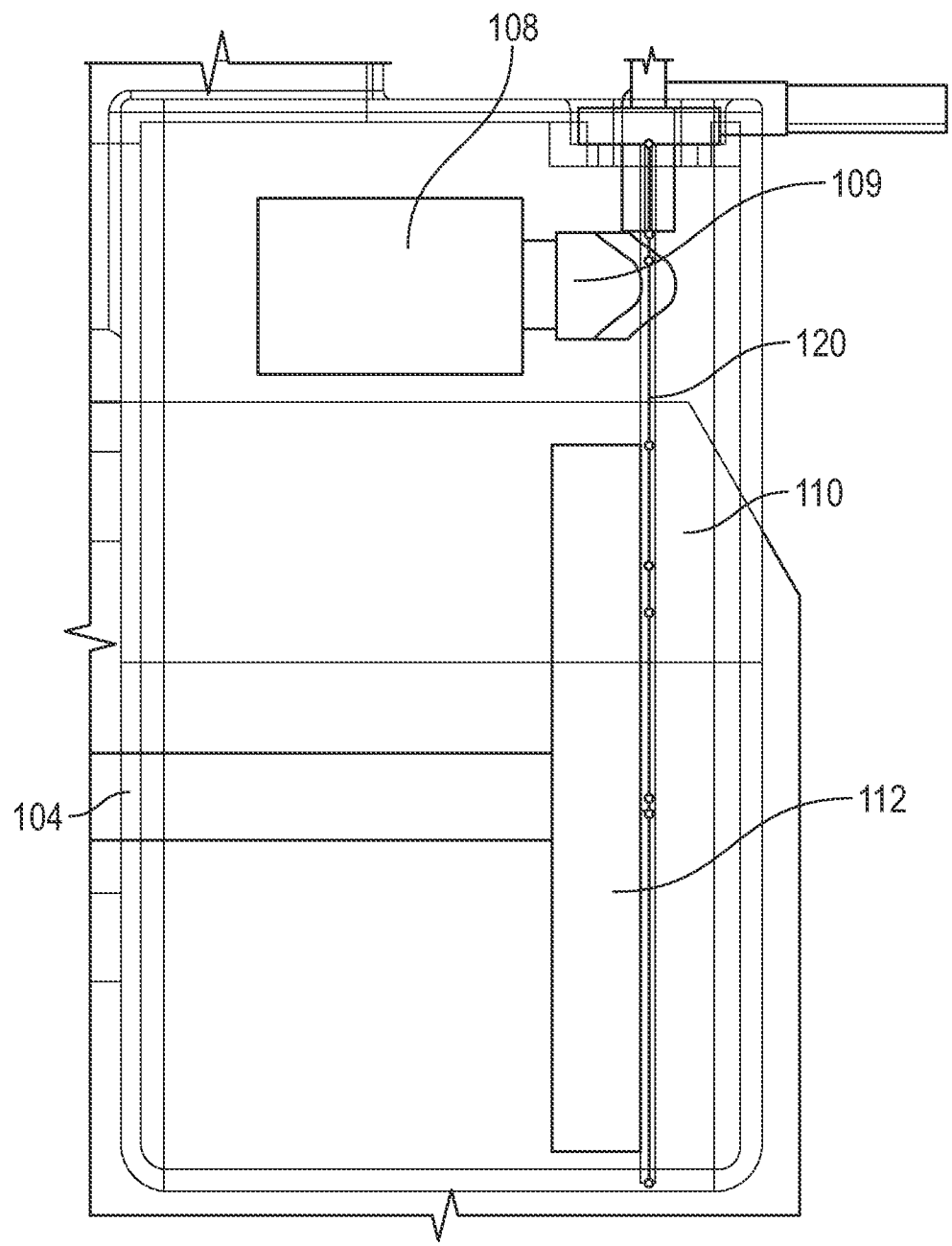
FIG. 3C is a zoomed in side view of the compounding platform of FIG. 1A with the pressing device in a fully extended position, in accordance with various aspects of the present disclosure.

FIG. 3A is a zoomed in side view of the compounding platform of FIG. 1A with a pressing device in an initial position, in accordance with various aspects of the present disclosure. FIG. 3B is a zoomed in side view of the compounding platform of FIG. 1A with the pressing device in a partially extended position, in accordance with various aspects of the present disclosure. FIG. 3C is a zoomed in side view of the compounding platform of FIG. 1A with the pressing device in a fully extended position, in accordance with various aspects of the present disclosure.

Referring to FIGS. 3A-3C, pressing face 112 may have an initial position (FIG. 3A), a partially retracted position (FIG. 3B), and a fully extended position (FIG. 3C). In the initial position, pressing device 105 retracts pressing face 112 such that pressing face 112 is disposed proximate proximal wall 113. In the initial position, pressing face 112 may be disposed within or may abut wall 113. As pressing face 112 transitions from the initial position to the partially extended position, pressive device 105 may extend pressing face 112 towards distal wall 115.

Pressing face 112 may be in the partially extended position when pressing face 112 is between the initial position and the fully extended position. In some embodiments, such as shown in FIG. 3B, when pressing face 112 is in the partially extended position and interior space 132 of bladder 130 is at least partially full of fluid, pressing face 112 abuts or contacts bladder 130. For example, bladder 130 may have received fluid from a fluid source (e.g., first vial 140 and/or second vial 160) such that interior space 132 expands in volume. Pressing face 112 may be in the partially extended position and may be disposed proximate bladder 130 such that interior space 132 expands to contact pressing face 112.

Pressing face 112 may be configured to prevent over expansion of interior space 132 of bladder 130. For example, pressing face 112 may be configured to provide an expansion limit of bladder 130 (e.g., interior space 132). Pressing face 112 may be positioned proximate bladder 130 such that as interior space 132 expands, it contacts pressing face 112 and thus is unable to expand anymore thereby restricting fluid from further entering interior space 132. In some embodiments, a user may set specific positions of pressing face 112 relative to bladder 130 to control the expansion limit of interior space 132, which thereby controls the volume of fluid that bladder 130 receives and holds.

In some embodiments, as shown in FIG. 3C, pressing face 112 may be in the fully extended position such that it abuts bladder 130 when interior space 132 is substantially devoid of fluid. Pressing device 105 may cause pressing face 112 to transition from the partially extended position (FIG. 3B) to the fully extended position (FIG. 3C). In some embodiment, pressing face 112 extending to the fully extended position causes pressing face 112 to press against bladder 130 causing interior space 132 to contract and thus drive fluid out of bladder 130. For example, pressing face 112 may transition to the fully extended position to cause pressing face 112 to press against bladder 130 to cause the fluid within interior space 132 to flow out of bladder 130 and cause interior space 132 to be substantially empty or devoid of fluid.

In some embodiments, compounding station 102 is configured to pull fluid into bladder 130 of consumable 120 such that interior space 132 fills up with fluid. For example, when consumable 120 is disposed within chamber 110, consumable 120 may substantially seal chamber 110. Valves 109a, 109b, 109c may be moved to an extended position thereby sealing flow paths 123, 127, and 125, respectively. When valves 109a, 109b, 109c are extended, they may press on flow paths 123, 127, and 125, respectively, sealing them. As described above, when valves 109a, 109b, 109c are retracted, flow paths 123, 127, and 125, respectively, are open and free to allow for the flow fluid or gas into and out of bladder 130.

To pull fluid into interior space 132 of bladder 130, the desired flow path out of flow paths 123, 127, and 125, is opened via the corresponding valve (e.g., valve 109a, 109b, 109c). The remaining flow paths may be closed. For example, valve 109a may be retracted and valve 109b and valve 109c may be extended resulting in flow path 123 being open and flow path 127 and 125 being closed. Flow path 123 being open may allow fluid to flow into interior space 132 via only flow path 123 and port 122.

In some embodiments, a vacuum is applied to chamber 110, which results in fluid being pulled into bladder 130 via port 122 and flow path 123. For example, pressure device 106 may generate a vacuum within chamber 110 by removing all the air within chamber 110. The generation of a vacuum within chamber 110 may cause chamber 110 and bladder 130 of consumable 120 to be at a lower pressure than a fluid source (e.g., first vial 140 and/or second vial 160) causing fluid to flow from the fluid source into interior space 132 of bladder 130.

In some embodiments, to control the volume of the fluid pulled into interior space 132 of bladder 130, pressing device 105 extends pressing face 112 such that pressing face 112 is positioned proximate bladder 130 to create an expansion limit (e.g., FIG. 3B). The position of pressing face 112, and the specific parameters of the vacuum generated with chamber 110 may be correlated to the amount of volume expected to flow into and fill interior space 132. In some embodiments, compounding platform 100 uses the correlation to adjust the position of pressing face 112 and generation of the vacuum within chamber 110, until the desired volume is pulled into interior space 132 of bladder 130.

In some embodiments, to push or drive fluid out of interior space 132 of bladder 130, the desired flow path out of flow paths 123, 127, and 125, is opened via the corresponding valve (e.g., valve 109a, 109b, 109c). The remaining flow paths may be closed. For example, valve 109b may be retracted and valve 109a and valve 109c may be extended resulting in flow path 127 being open and flow path 123 and 125 being closed. Flow path 127 being open may allow fluid to flow out of interior space 132 via only flow path 127 and port 126. In some embodiments, to push or drive fluid out of interior space 132, pressing device 105 extends pressing face 112 (e.g., to the fully extended position) against bladder 130 to apply a force to interior space 132 to cause interior space 132 to retract thereby forcing fluid out of the opened flow path (e.g., flow path 127) and out of the port in fluid communication with the one flow path (e.g., port 126). In some embodiments, the volume of fluid displaced or removed from interior space 132 of bladder 130 is correlated with the change in position of pressing face 112.

Figure 4A:
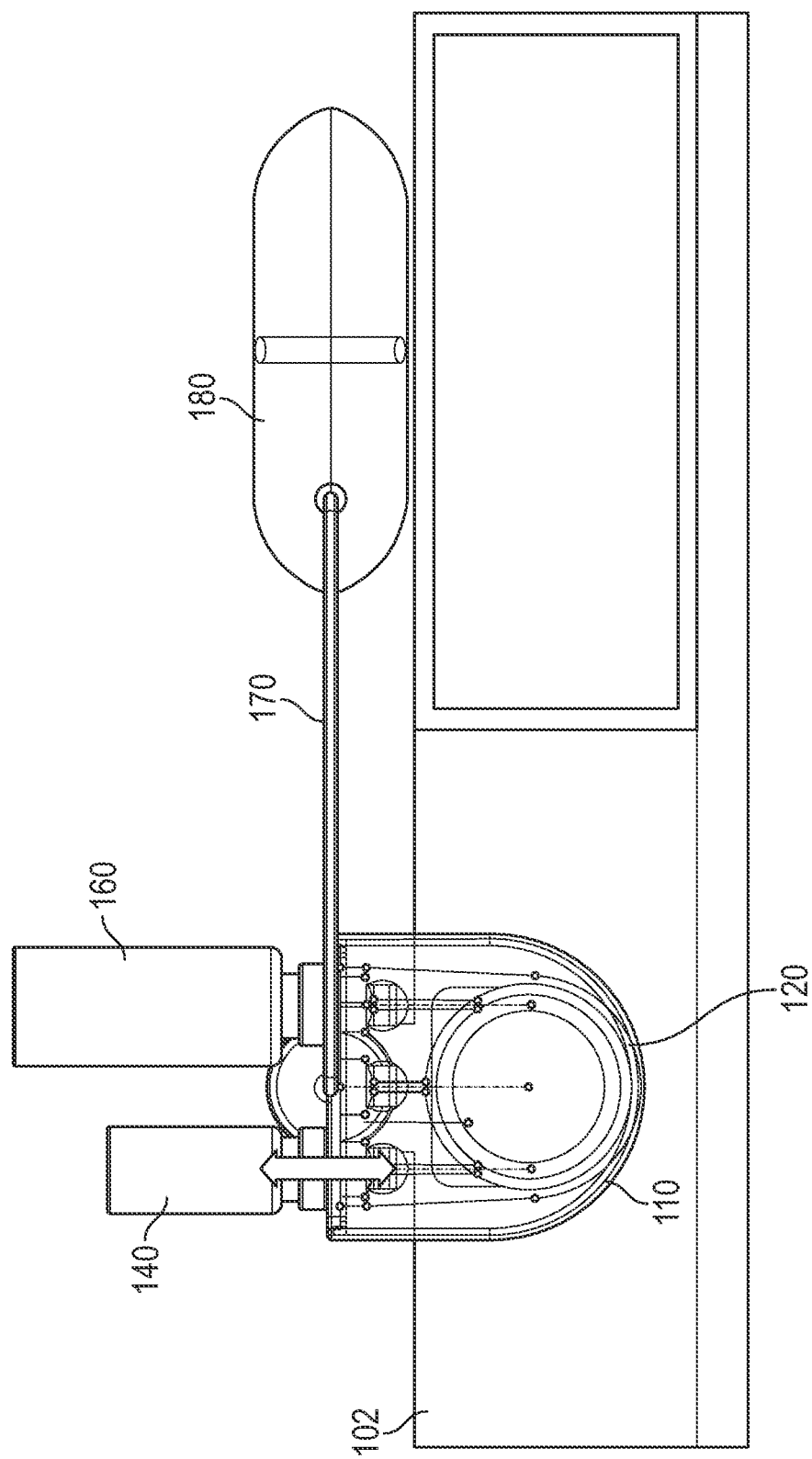
FIG. 4A is a front view of the compounding platform of FIG. 1A with the compounding platform in use, in accordance with various aspects of the present disclosure.
Figure 4B:
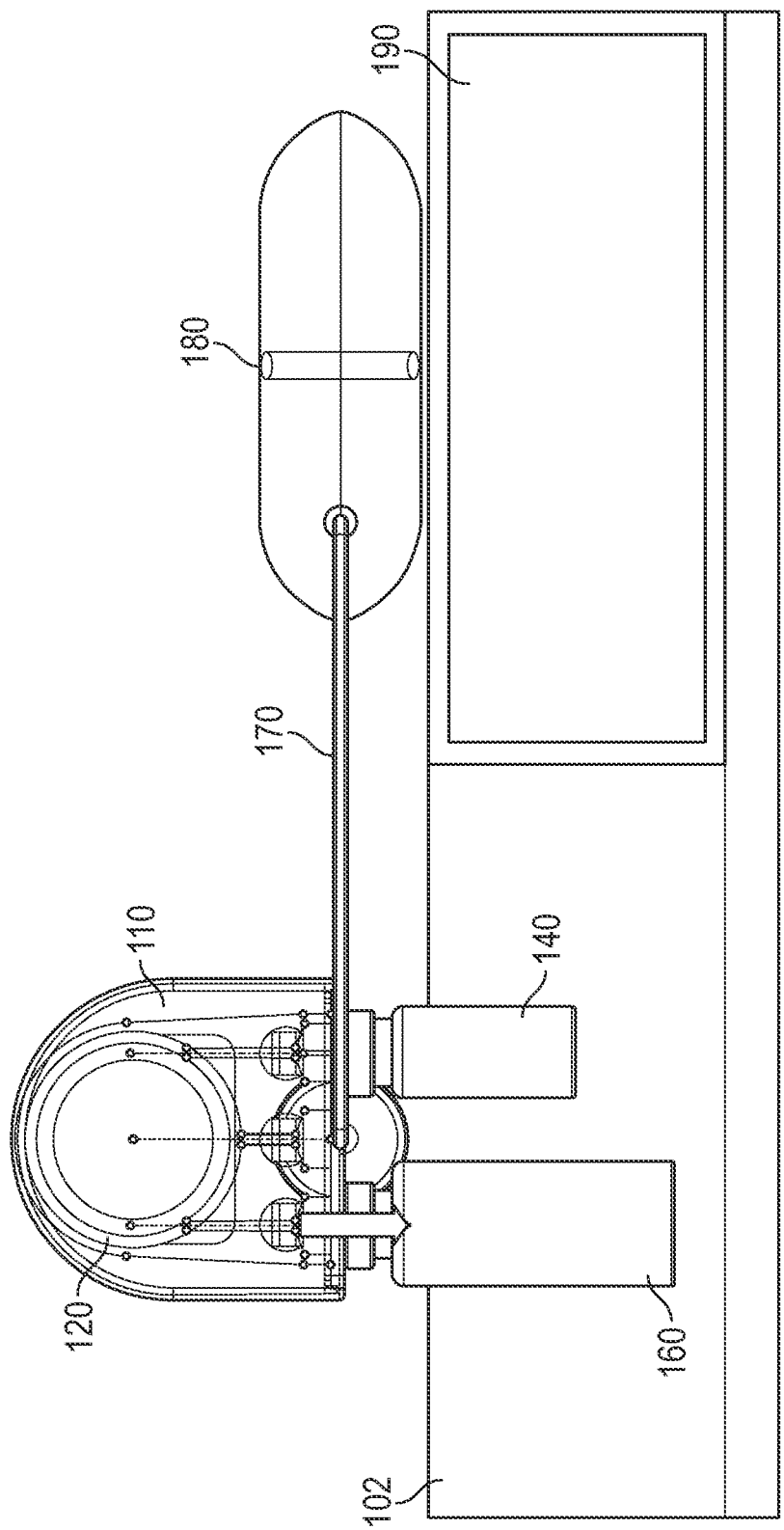
FIG. 4B is a front view of the compounding platform of FIG. 1A with the compounding platform in use, in accordance with various aspects of the present disclosure.
Figure 4D:
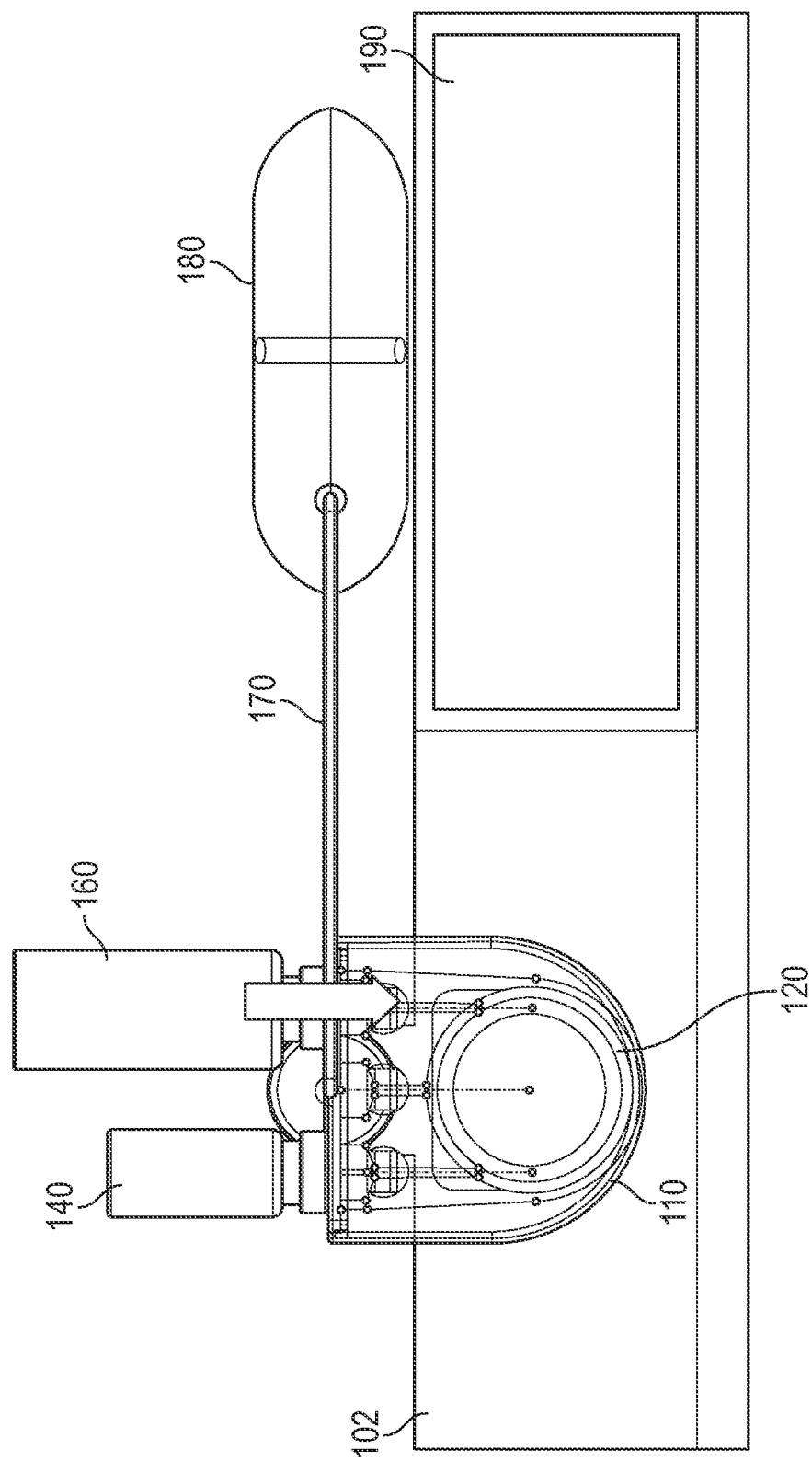
FIG. 4D is a front view of the compounding platform of FIG. 1A with the compounding platform in use, in accordance with various aspects of the present disclosure.

FIG. 4A is a front view of the compounding platform of FIG. 1A with the compounding platform in use, in accordance with various aspects of the present disclosure. FIG. 4B is a front view of the compounding platform of FIG. 1A with the compounding platform in use, in accordance with various aspects of the present disclosure. FIG. 4C is a front view of the compounding platform of FIG. 1A with the compounding platform in use, in accordance with various aspects of the present disclosure. FIG. 4D is a front view of the compounding platform of FIG. 1A with the compounding platform in use, in accordance with various aspects of the present disclosure.

Referring to FIGS. 4A-4D, compounding platform 100 may be configured to reconstitute a drug vial, such as second vial 160. For example, compounding platform 100 may allow for the adjusting of ratios of a diluent and drug (e.g., medicament) within a vial or fluid container.

In some embodiments, consumable 120 is inserted through slot 121 of chamber 110 to secure consumable 120 within chamber 110. A user may interact with user interface 190 to select a desired routine or program for compounding platform 100 to run to achieve the desired results. For example, a user may interact with user interface 190 to select a routing directed to reconstituting a vial. Compounding platform 100 may then go through an automated or semi-automated process to reconstitute a vial.

Reconstituting a vial (e.g., second vial 160) requires fluid to flow from one or more vials into bladder 130 and from bladder 130 into the one or more vials. The reconstituted fluid is may then be transferred from the bladder 130 to one or more vials and/or storage containers (e.g., delivery bag 180).

In some embodiments, one or more of valves 109a, 109b, 109c are closed to close one or more of flow paths 123, 127, and 125. For example, valve 109b and valve 109c may be closed and valve 109a may be opened. This results in fluid being able to flow into port 122 and through flow path 123, while fluid is prevented from flowing into port 126 and port 124 and through flow path 127 and 125, respectively. A vacuum may be applied within chamber 110 by pressure device 106 causing a volume of air to be pulled into interior space 132 of bladder 130. The vacuum may then be removed from chamber 110.

In some embodiments, first vial 140 is coupled to port 122 and second vial 160 is coupled to port 124. First vial 140 may be a fluid source of diluent fluid and second vial 160 may be a fluid source of a drug, such as a lyophilized drug source. Delivery bag 180 may disposed on storage area 185 of compounding station 102 and may be coupled to port 126 via delivery tubing 170.

Compounding station 102 may be configured to conduct a series of push and pull routines or maneuvers to transfer fluid between first vial 140 and/or second vial 160 and bladder 130. For example, compounding station 102 may open one or more valves (e.g. valves 109a, 109b, 109c) and rotation chamber 110 to allow fluid to flow between first vial 140 and/or second vial 160 and bladder 130.

In some embodiments, interior space 132 includes a volume of air due to the vacuum generated within chamber 110, which resulted in air flowing into bladder 130. Pressing face 112 may be extended by pressing device 105 to cause pressing face 112 to apply a pressure to the partially expanded with air interior space 132. Due to valve 109a being opened, the air from interior space 132 may be driven out of bladder 130 via flow path 123 and through port 122 into first vial 140. Fluid, such as diluent fluid, from first vial 140 may be driven from first vial 140 into interior space 132 through port 122 and flow path 123 due to the air being driven out of bladder 130 and into first vial 140 causing fluid to be displaced from first vial 140 and into bladder 130. In other words, as illustrated in FIG. 4A, air may be driven from interior space 132 into first vial 140 causing fluid to be driven from first vial 140 into interior space 132.

With reference to FIG. 4B, the diluent fluid from first vial 140 may be transferred from first vial 140 and disposed within interior space 132, and then transferred from interior space 132 to second vial 160. For example, chamber 110 may be rotated or inverted by rotating device 107 causing chamber 110 to be in an inverted position (e.g., rotated 180 degrees) from the baseline position. Prior to rotation or inversion of chamber 110, valve 109c may be opened and valve 109a and valve 109b may be closed resulting in second vial 160 being in fluid communication with bladder 130 through port 124 and flow path 125 and first vial 140 no longer being in fluid communication with bladder 130.

Once chamber 110 has been inverted or rotated substantially 180 degrees, the diluent fluid may flow from interior space 132 through flow path 125 and port 124 and into second vial 160. Second vial 160 may contain a drug or medicament. The drug or medicament disposed within second vial 160 may be configured to dissolve within a diluent fluid, such as the diluent fluid disposed within first vial 140. In some embodiments, a vacuum is generated within chamber 110 and/or pressing device 105 causes pressing face 112 to press against bladder 130 and retract from pressing against bladder 130 to cause the diluent fluid within bladder 130 to flow into second vial 160.

In some embodiments, transfer of the diluent fluid from interior space 132 to second vial 160 causes air that had been transferred to first vial 140 to transfer back into interior space 132 resulting in second vial 160 at least partially including the diluent fluid and interior space 132 at least partially including air (e.g., from first vial 140). Transfer of the diluent fluid from interior space 132 to second vial 160 may cause air from second vial 160 that is displaced by the diluent fluid to transfer into interior space 132 resulting in second vial 160 at least partially including the diluent fluid and interior space 132 at least partially including air (e.g., from second vial 160).

In some embodiments, multiple inversions and/or rotations are required to fully transfer the diluent fluid from interior space 132 to second vial 160. Delivery tube 170 may be coupled to consumable 120 and configured to allow for multiple rotations of chamber 110 and consumable 120 without being damaged. For example, delivery tube 170 may have a predetermined length that allow for multiple rotations of chamber 110 and consumable 120 without delivery tube 170 getting twisted and damaged. In some embodiments, delivery tube 170 includes a pre-twisted section to assist with minimizing unwanted twisting and damage to delivery tube 170.

With reference to FIG. 4C, upon inversion of chamber 110 and flow of diluent fluid into second vial 160, rotating device 107 may be configured to rotate or oscillate chamber 110. For example, rotating device 107 may rotate chamber 110 clockwise a predetermined amount and then rotate chamber 110 counter clockwise a predetermined amount. Rotation or oscillation of chamber 110 may cause shaking or mixing of substances within second vial 160 due to second vial 160 being coupled to consumable 120, which is disposed within chamber 110. For example, oscillation of chamber 110 may cause mixing of the diluent fluid and medicament within second vial 160 causing the medicament to fully dissolve within the diluent fluid and create reconstituted fluid. In some embodiments, valves 109a, 109b, 109c are closed to prevent the reconstituted fluid from flowing from second vial 160 into bladder 130 during oscillation of chamber 110.

With chamber 110 being 180 degrees from the baseline position and after flow of the diluent fluid into second vial 160, rotating device 107 may oscillate or rock chamber 110 from between 180 degrees and 270 degrees to between 180 degrees and 90 degrees. In some embodiments, rotating device 107 oscillates chamber 110 from any position between 0 degrees and 360 degrees from the baseline position of chamber 110 causing the medicament to fully dissolve within the diluent fluid within second vial 160 and create reconstituted fluid.

With reference to FIG. 4D, upon oscillation of chamber 110 and dissolving of the medicament within the diluent fluid within second vial 160, chamber 110 may return to the baseline position. Upon chamber 110 returning to the baseline position, valve 109c may be opened allowing the reconstituted fluid from second vial 160 flows into bladder 130 via port 124 and flow path 125. The air from interior space 132 may be displaced by the reconstituted fluid and may flow into second vial 160. In some embodiments, a vacuum is generated within chamber 110 and/or pressing device 105 causes pressing face 112 to press against bladder 130 and retract from pressing against bladder 130 to cause the reconstituted fluid within second vial 160 to flow into bladder 130.

Figure 5:
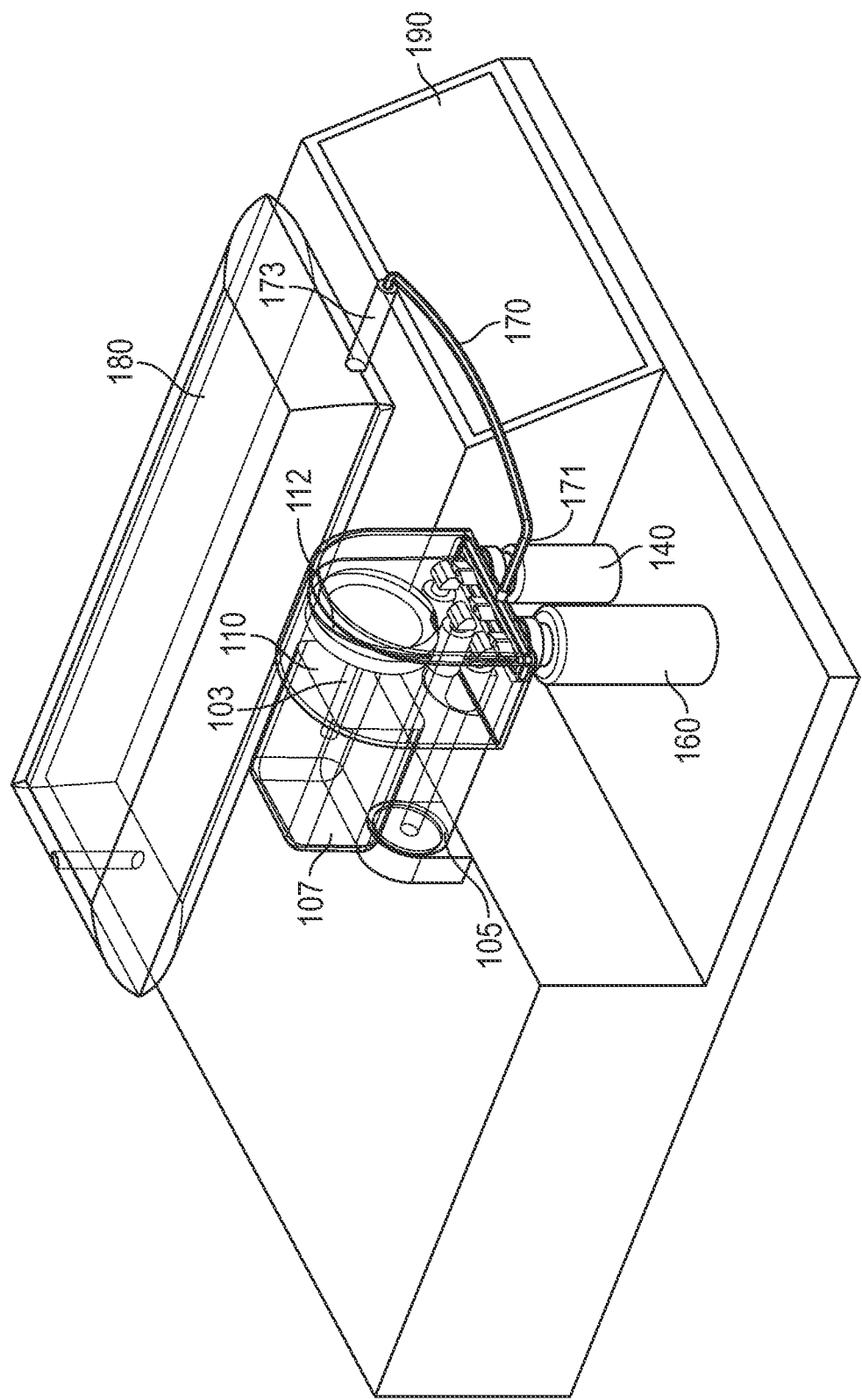
FIG. 5 is a front perspective view of the compounding platform of FIG. 1A with the compounding platform in use, in accordance with various aspects of the present disclosure.

FIG. 5 is a front perspective view of the compounding platform of FIG. 1A with the compounding platform in use, in accordance with various aspects of the present disclosure.

Referring to FIG. 5, the reconstituted fluid disposed within bladder 130 may be transferred to delivery bag 180 via delivery tubing 170. For example, upon the reconstituted fluid being transferred to interior space 132, valve 109c may extend to close flow path 125 and prevent fluid flow through port 124 and flow path 125. Valve 109b may retract to open flow path 127 to allow fluid to flow from interior space 132 through flow path 127 and port 126 to delivery bag 180 coupled to port 126 via delivery tubing. In some embodiments, a vacuum is generated within chamber 110 and/or pressing device 105 causes pressing face 112 to press against bladder 130 and retract from pressing against bladder 130 to cause the reconstituted fluid within interior space 132 to flow into delivery bag 180 via delivery tubing 170.

In some embodiments, chamber 110 is rotated prior to causing the reconstituted fluid to transfer to delivery bag 180. For example, chamber 110 may be rotated substantially 180 degrees from the baseline position and the reconstituted fluid may be transferred from interior space 132 to delivery bag 180. Inversion of chamber 110 prior to transferring of the reconstituted fluid to delivery bag 180 may prevent or minimize air entering delivery bag 108.

In some embodiments, delivery tubing 170 includes first end 171 coupled to consumable 120 and second end 173 coupled to delivery bag 180. Second end 173 may include a male luer coupling delivering tubing 170 to delivery bag 180. In some embodiments, to facilitate handling of hazardous drugs, second end 173 is provided with or an interface to leak proof or leak free drug transfer device, such as a closed system drug-transfer device (CSTD). For example, if one or more of first vial 140 and/or second vial 160 include hazardous material, to prevent injury to individuals around compounding platform 100, second 173 may include a leak proof or leak free drug transfer device to prevent leaking of the hazardous material when delivery tubing 170 is decoupled from delivery bag 180.

In some embodiments, second end 173 includes a hazardous drug safety needle. For example, second end 173 may include a ballpoint safety needle intended to protect a health care during decoupling of second 173 from delivery bag 180. In some embodiment, the ballpoint safety needled includes a spring and a protective ballpoint that is disposed over a needle. The spring may be extended such that the protective ballpoint covers the tip of the needle. The protective ballpoint may be retracted by application of a force to expose the needle. Upon removal of the force, the protective ballpoint may extend to cover the tip of the needle due to the spring being biased to be extended.

In some embodiments, consumable 120 is disposable. For example, consumable 120 may be one time use to allow a user to discard consumable 120 upon completion of the desired task (e.g., creation of a reconstituted fluid and transfer of to the reconstituted fluid to delivery bag 180). In some embodiments, upon decoupling of second end 173 from delivery bag 180, consumable 120 is discarded along with first vial 140, second vial 160, and/or delivery tube 170. Consumable 120 may be discarded along with first vial 140, second vial 160, and/or delivery tube 170 if the drug or medicament originally stored within second vial 160 is hazardous. In some embodiments, upon transfer of the reconstituted fluid from second vial 160 to bladder 130, consumable 120 may be removed from chamber 110 and stored in a secure location for use later.

In some embodiments, compounding platform 100 is configured to create a reconstituted fluid for transfer to delivery bag 180. For example, using series of extensions and retractions of valves 109a, 109b, 109c, with chamber 110 in the baseline position, diluent fluid may be transferred from first vial 140 to interior space 132 and medicament from second vial 160 may be transferred from second vial 160 to interior space 132. In some embodiments, the diluent fluid and the medicament are transferred simultaneously to interiors space 132. Upon transfer of the diluent fluid and the medicament to interior space 132, chamber 110 may be rotated and/or oscillated by rotating device 107 to cause the medicament to dissolve within the diluent fluid to create reconstituted fluid within interior space 132.

In some embodiments, upon create of the reconstituted fluid, the reconstituted fluid may be transferred to delivery bag 180 via delivery tubing 170. Prior to transfer of the reconstituted fluid to delivery bag 180, chamber 110 may be inverted to prevent air from transferring to delivery bag 180.

In some embodiments, delivery bag 180 is empty prior to transferring fluid from bladder 130 to delivery bag 180. Alternatively, delivery bag 180 may include a fluid, such as saline, that is configured to mix with the reconstituted fluid upon transfer of the reconstituted fluid from bladder 130 to delivery bag 180.

The disclosures described herein include at least the following clauses:

Clause 1: A compounding platform comprising a compounding station including a user interface configured to receive inputs from a user and a rotating device, a chamber coupled to the compounding station, wherein the rotating device is coupled to the chamber and configured to rotate the chamber relative to the compounding station, a consumable configured to be disposed within the chamber, the consumable including a plurality of ports and a bladder in fluid communication with the plurality of ports, a first vial removably coupled to the consumable via a first port of the plurality of ports, the first vial including a diluent fluid, a second vial removably coupled to the consumable via a second port of the plurality of ports, the second vial including a medicament, and a plurality of valves configured to control fluid flow into and out of the bladder, wherein the plurality of valves correspond to the plurality of ports.

Clause 2: The compounding platform of claim 1, wherein the consumable includes a scaling element configured to allow the bladder to be in communication with the plurality of ports.

Clause 3: The compounding platform of claim 2, wherein the chamber includes a slot and the consumable is disposed through the slot such that the sealing element engages with the slot to secure the bladder within the chamber.

Clause 4: The compounding platform of claim 3, wherein the chamber is airtight upon inserting the consumable through the slot and disposing the sealing element within the slot.

Clause 5: The compounding platform of claim 2, wherein the sealing element includes the first port and the second port.

Clause 6: The compounding platform of claim 1, wherein the bladder includes a first flow path in fluid communication with the first port and a second flow path in communication with the second port.

Clause 7: The compounding platform of claim 6, wherein the plurality of valves includes a first valve and a second valve, the first valve configured to block flow within the first flow path and the second valve configured to block flow within the second flow path.

Clause 8: The compounding platform of claim 6, wherein the first flow path is in fluid communication with the first vial when the first vial is coupled to the first port.

Clause 9: The compounding platform of claim 6, wherein the second flow path is in fluid communication with the second vial when the second vial is coupled to the second port.

Clause 10: The compounding platform of claim 1 further comprising:
a delivery bag removably coupled to the consumable via a third port of the plurality of ports.

Clause 11: The compounding platform of claim 10, wherein the third port is coupled to a delivery tube, the delivery tube coupling the delivery bag to the third port.

Clause 12: The compounding platform of claim 1 further comprising a pressure device coupled to the chamber, the pressure device configured to generate a vacuum within the chamber.

Clause 13: The compounding platform of claim 1 further comprising a pressing device coupled to the chamber, the pressing device including a pressing face disposed within the chamber, the pressing device having a retracted position and an extended position, wherein in the extended position, the pressing device is proximate the bladder compared to when the pressing device is in the retracted position.

Clause 14: The compounding platform of claim 1, wherein the chamber is a vacuum chamber.

Clause 15: The compounding platform of claim 1, wherein the first port and the second port allow for two-way fluid communication.

Clause 16: The compounding platform of claim 1, wherein the bladder includes an interior space in fluid communication with the first vial and the second vial.

Clause 17: The compounding platform of claim 1 further comprising a controller disposed within the compounding station and communicatively coupled to the user interface, the controller configured to cause the compounding station to perform a set of maneuvers in response to the inputs received via the user interface, wherein the set of maneuvers includes one or more of rotation of the chamber, opening of one of the plurality of valves, and generation of a vacuum within the chamber.

Clause 18: The compounding platform of claim 1, wherein the rotating device rotates the chamber from 0 degrees to 360 degrees from a baseline position relative to the compounding station.

Clause 19: A compounding platform comprising a compounding station including a user interface configured to receive inputs from a user and a rotating device, a chamber coupled to the compounding station and having a slot, wherein the rotating device is coupled to the chamber and rotates the chamber from 0 degrees to 360 degrees from a baseline position relative to the compounding station, a consumable configured to be disposed within the chamber, the consumable including a sealing element, a plurality of ports, and a bladder in fluid communication with the plurality of ports, wherein the chamber includes a slot and the consumable is disposed through the slot such that the sealing element engages with the slot to secure the bladder within the chamber, a first vial removably coupled to the consumable via a first port of the plurality of ports, the first vial including a diluent fluid, a second vial removably coupled to the consumable via a second port of the plurality of ports, the second vial including a medicament, wherein the bladder includes an interior space in fluid communication with the first vial and the second vial, a plurality of valves configured to control fluid flow into and out of the bladder, wherein the plurality of valves correspond to the plurality of ports, a pressing device coupled to the chamber, the pressing device including a pressing face disposed within the chamber, the pressing device having a retracted position and an extended position, wherein in the extended position, the pressing device is proximate the bladder compared to when the pressing device is in the retracted position, a pressure device coupled to the chamber, the pressure device configured to generate a vacuum within the chamber, and a delivery bag removably coupled to the consumable via a third port of the plurality of ports, wherein the bladder includes a first flow path in fluid communication with the first port and a second flow path in communication with the second port, and the plurality of valves includes a first valve and a second valve, the first valve configured to block flow within the first flow path and the second valve configured to block flow within the second flow path.

Clause 20: A method of compounding a medical fluid, the method comprising inserting a consumable through a slot of a chamber to dispose the consumable within the chamber, the consumable including a bladder configured to expand, generating a vacuum within the chamber to cause an inflow of air to enter the consumable through a first port, removably coupling a first vial the chamber, the first vial containing a medicament fluid and being in fluid communication with the first port of the consumable when coupled to the chamber to allow the medicament fluid to flow from the first vial to the bladder, rotating the chamber to cause the air from the consumable to flow into the first vial via the first port, which causes a predetermined amount of the medicament fluid to flow from the first vial into the consumable, and closing the first port and opening a second port coupled to a delivery bag such that the predetermined amount of medicament fluid flows through the second port to the delivery bag.

Clause 21: A method of reconstituting a medical fluid, the method comprising generating a vacuum within a chamber, the chamber coupled to a compounding station and including a consumable having a first port and a second port, wherein the generation of the vacuum causes an inflow of air to enter the consumable and the first port and the second port are in fluid communication with the consumable, removing the vacuum from the chamber and opening a first valve of a plurality of valves to cause the air to flow from the consumable into a first vial resulting in diluent fluid flowing from the first vial to the consumable through the first port, the first vial coupled to the first port such that the first vial is in fluid communication with the consumable when the first valve is opened, rotating the chamber, via a rotating device coupling the chamber to the compounding state, such that the chamber is substantially inverted from a baseline position, in response to rotating the chamber, opening a second valve of the plurality of valves to cause the diluent fluid to flow from the consumable to a second vial, the second vial coupled to the second port such that the second vial is in fluid communication with the consumable when the second valve is opened, the second vial including a medicament, oscillating the chamber, via the rotating device, such that that second vial is oscillated causing the medicament to at least partially dissolve in the diluent fluid within the second vial to create a reconstituted fluid, and rotating the chamber, via the rotating device, to the baseline position causing the reconstituted fluid to flow from the second vial to the consumable via the second port.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A compounding platform comprising:
a compounding station including a user interface configured to receive inputs from a user and a rotating device;
a chamber coupled to the compounding station, wherein the rotating device is coupled to the chamber and configured to rotate the chamber relative to the compounding station;
a consumable configured to be disposed within the chamber, the consumable including a plurality of ports and a bladder in fluid communication with the plurality of ports;
a first vial removably coupled to the consumable via a first port of the plurality of ports, the first vial including a diluent fluid;
a second vial removably coupled to the consumable via a second port of the plurality of ports, the second vial including a medicament; and
a plurality of valves configured to control fluid flow into and out of the bladder, wherein the plurality of valves correspond to the plurality of ports.

2. The compounding platform of claim 1, wherein the consumable includes a sealing element configured to allow the bladder to be in communication with the plurality of ports.

3. The compounding platform of claim 2, wherein the chamber includes a slot and the consumable is disposed through the slot such that the sealing element engages with the slot to secure the bladder within the chamber.

4. The compounding platform of claim 3, wherein the chamber is airtight upon inserting the consumable through the slot and disposing the sealing element within the slot.

5. The compounding platform of claim 2, wherein the sealing element includes the first port and the second port.

6. The compounding platform of claim 1, wherein the bladder includes a first flow path in fluid communication with the first port and a second flow path in communication with the second port.

7. The compounding platform of claim 6, wherein the plurality of valves includes a first valve and a second valve, the first valve configured to block flow within the first flow path and the second valve configured to block flow within the second flow path.

8. The compounding platform of claim 6, wherein the first flow path is in fluid communication with the first vial when the first vial is coupled to the first port.

9. The compounding platform of claim 6, wherein the second flow path is in fluid communication with the second vial when the second vial is coupled to the second port.

10. The compounding platform of claim 1 further comprising:
a delivery bag removably coupled to the consumable via a third port of the plurality of ports.

11. The compounding platform of claim 10, wherein the third port is coupled to a delivery tube, the delivery tube coupling the delivery bag to the third port.

12. The compounding platform of claim 1 further comprising:
a pressure device coupled to the chamber, the pressure device configured to generate a vacuum within the chamber.

13. The compounding platform of claim 1 further comprising:
a pressing device coupled to the chamber, the pressing device including a pressing face disposed within the chamber, the pressing device having a retracted position and an extended position, wherein in the extended position, the pressing device is proximate the bladder compared to when the pressing device is in the retracted position.

14. The compounding platform of claim 1, wherein the chamber is a vacuum chamber.

15. The compounding platform of claim 1, wherein the first port and the second port allow for two-way fluid communication.

16. The compounding platform of claim 1, wherein the bladder includes an interior space in fluid communication with the first vial and the second vial.

17. The compounding platform of claim 1 further comprising:
a controller disposed within the compounding station and communicatively coupled to the user interface, the controller configured to cause the compounding station to perform a set of maneuvers in response to the inputs received via the user interface, wherein the set of maneuvers includes one or more of rotation of the chamber, opening of one of the plurality of valves, and generation of a vacuum within the chamber.

18. The compounding platform of claim 1, wherein the rotating device rotates the chamber from 0 degrees to 360 degrees from a baseline position relative to the compounding station.

19. A compounding platform comprising:
a compounding station including a user interface configured to receive inputs from a user and a rotating device;
a chamber coupled to the compounding station and having a slot, wherein the rotating device is coupled to the chamber and rotates the chamber from 0 degrees to 360 degrees from a baseline position relative to the compounding station;
a consumable configured to be disposed within the chamber, the consumable including a sealing element, a plurality of ports, and a bladder in fluid communication with the plurality of ports, wherein the chamber includes a slot and the consumable is disposed through the slot such that the sealing element engages with the slot to secure the bladder within the chamber;
a first vial removably coupled to the consumable via a first port of the plurality of ports, the first vial including a diluent fluid;
a second vial removably coupled to the consumable via a second port of the plurality of ports, the second vial including a medicament, wherein the bladder includes an interior space in fluid communication with the first vial and the second vial;
a plurality of valves configured to control fluid flow into and out of the bladder, wherein the plurality of valves correspond to the plurality of ports;
a pressing device coupled to the chamber, the pressing device including a pressing face disposed within the chamber, the pressing device having a retracted position and an extended position, wherein in the extended position, the pressing device is proximate the bladder compared to when the pressing device is in the retracted position;
a pressure device coupled to the chamber, the pressure device configured to generate a vacuum within the chamber; and
a delivery bag removably coupled to the consumable via a third port of the plurality of ports,
wherein the bladder includes a first flow path in fluid communication with the first port and a second flow path in communication with the second port, and the plurality of valves includes a first valve and a second valve, the first valve configured to block flow within the first flow path and the second valve configured to block flow within the second flow path.

* * * * *